(12) United States Patent
Kaib et al.

(10) Patent No.: US 10,578,677 B2
(45) Date of Patent: Mar. 3, 2020

(54) SYSTEMS AND METHODS FOR MONITORING BATTERY LIFE STATUS

(71) Applicant: ZOLL Medical Corporation, Chelmsford, MA (US)

(72) Inventors: Thomas E. Kaib, Irwin, PA (US); John Macho, Pittsburgh, PA (US); Shane Volpe, Saltsburg, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 659 days.

(21) Appl. No.: 15/195,339

(22) Filed: Jun. 28, 2016

(65) Prior Publication Data

US 2017/0003356 A1 Jan. 5, 2017

Related U.S. Application Data

(60) Provisional application No. 62/186,674, filed on Jun. 30, 2015.

(51) Int. Cl.
*A61N 1/37* (2006.01)
*G01R 31/392* (2019.01)
*A61N 1/39* (2006.01)

(52) U.S. Cl.
CPC ......... *G01R 31/392* (2019.01); *A61N 1/3708* (2013.01); *A61N 1/3925* (2013.01); *A61B 2560/0204* (2013.01)

(58) Field of Classification Search
CPC . A61N 1/3708; A61B 5/6805; G01R 31/3679
USPC ......................................................... 607/116
See application file for complete search history.

(56) References Cited

U.S. PATENT DOCUMENTS

| 4,928,690 A | 5/1990 | Heilman et al. |
| 5,078,134 A | 1/1992 | Heilman et al. |
| 5,741,306 A * | 4/1998 | Glegyak .................. A61N 1/39 607/12 |
| 5,944,669 A | 8/1999 | Kaib |
| 6,065,154 A | 5/2000 | Hulings et al. |
| 6,253,099 B1 | 6/2001 | Oskin et al. |

(Continued)

OTHER PUBLICATIONS

"Battery life and how to improve it: Battery Life (and Death)"; Battery and Energy Technologies; http://www.mpoweruk.com/life.htm, 11 pages.

(Continued)

*Primary Examiner* — Nadia A Mahmood
(74) *Attorney, Agent, or Firm* — The Webb Law Firm

(57) ABSTRACT

An external medical device includes a battery that can support a plurality of charge-discharge cycles prior to a predetermined battery life threshold. The device also includes a battery circuit that is operative for monitoring a condition of the battery, determining a battery life status of the battery based on the monitored condition and the predetermined battery life threshold, and, responsive to the determined battery life status, causing the device to enter into a low power operating mode. The low power operating mode can include modifying device functions that are performed, or modifying the manner in which a capacitor of the device is charged, or changing the battery that charges the capacitor, or isolating the capacitor from charge drainage, or causing the device to operate from charge stored on the capacitor.

18 Claims, 15 Drawing Sheets

(56) References Cited

U.S. PATENT DOCUMENTS

| | | | |
|---|---|---|---|
| 6,280,461 B1 | 8/2001 | Glegyak et al. | |
| 6,681,003 B2 | 1/2004 | Linder et al. | |
| 8,271,082 B2 | 9/2012 | Donnelly et al. | |
| 8,369,944 B2 | 2/2013 | Macho et al. | |
| 8,909,335 B2 | 12/2014 | Radzelovage | |
| 2012/0274280 A1* | 11/2012 | Yip | H02J 7/0014 320/112 |
| 2013/0245973 A1* | 9/2013 | Ross, Jr. | H01M 10/48 702/63 |
| 2015/0039039 A1 | 2/2015 | Macho et al. | |
| 2015/0039042 A1 | 2/2015 | Amsler et al. | |

OTHER PUBLICATIONS

"Smart Battery Data Specification", Smart Battery System Specifications, Copyright(C) 1996, 1997 1998, Benchmarq Microelectronics Inc., Duracel Inc., Energizer Power Systems, Intel Corporation, Linear Technology, Maxim Integrated Products, Mitsubishi Electric Corporation, National Semiconductor Corporation, Toshiba Battery Co., Varta Batterie AG, Dec. 11, 1998, 54 pages, Revision 1.1.
"Smart Battery"; http://en.wikipedia.org/wiki/Smart_Battery, 2 pages.
"Supercapacitor"; https://en.wikipedia.org/wiki/Supercapacitor, 35 pages.

* cited by examiner

| BATTERY TEST RESULTS | | |
|---|---|---|
| # | INTERNAL RESISTANCE | FLAG DATE |
| 20 | 0.421 | 01/05/2015 |
| 19 | 0.393 | 12/28/2014 |
| 18 | 0.395 | 12/21/2014 |
| 17 | 0.382 | 12/12/2014 |
| 16 | 0.380 | 12/04/2014 |
| 15 | 0.387 | 11/26/2014 |
| 14 | 0.392 | 11/18/2014 |
| 13 | 0.384 | 11/10/2014 |
| 12 | 0.388 | 11/02/2014 |
| 11 | 0.379 | 10/25/2014 |
| 10 | 0.377 | 10/17/2014 |
| 9 | 0.368 | 09/12/2014 |
| 8 | 0.327 | 09/05/2014 |
| 7 | 0.336 | 08/28/2014 |
| 6 | 0.344 | 08/20/2014 |
| 5 | 0.334 | 08/12/2014 |
| 4 | 0.363 | 07/01/2014 |
| 3 | 0.355 | 06/23/2014 |
| 2 | 0.343 | 06/15/2014 |
| 1 | 0.363 | 06/07/2014 |

FIG. 8

SYSTEMS AND METHODS FOR MONITORING BATTERY LIFE STATUS

CROSS REFERENCE TO RELATED APPLICATIONS

This application claims priority to U.S. Provisional Patent Application No. 62/186,674, filed Jun. 30, 2015, the disclosure of which is hereby incorporated in its entirety by reference.

BACKGROUND

Technical Field

The present disclosure relates to an external medical device and, in particular, to an external medical device configured to monitor battery conditions to determine battery life status.

Description of Related Art

There are a wide variety of electronic and mechanical devices for monitoring and/or treating patients' medical conditions. In some examples, depending on the underlying medical condition being monitored or treated, medical devices, such as cardiac monitors, pacemakers, and defibrillators may be surgically implanted or connected externally to the patient. In some cases, physicians may use medical devices alone or in combination with drug therapies to treat patient medical conditions.

One of the most deadly cardiac arrhythmias is ventricular fibrillation, which occurs when the normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

SUMMARY

Various preferred and non-limiting examples of the present invention will now be described and set forth in the following numbered clauses.

Clause 1: In an example, an external medical device comprises: a battery that can support a plurality of charge-discharge cycles prior to a predetermined battery life threshold; and a battery circuit operative for: monitoring a condition of the battery; determining a battery life status of the battery based on the monitored condition and the predetermined battery life threshold; and responsive to the determined battery life status, causing the device to enter into a low power operating mode.

Clause 2: The external medical device of clause 1, wherein the device can further comprise a battery receptacle configured to receive the battery.

Clause 3: The external medical device of clauses 1 or 2, wherein the battery can be replaceable.

Clause 4: The external medical device of any one of clauses 1-3, wherein monitoring the condition of the battery can comprise monitoring an internal resistance of the battery.

Clause 5: The external medical device of any one of clauses 1-4, wherein the device can further comprise a wearable medical device.

Clause 6: The external medical device of any one of clauses 1-5, wherein the device can further comprise a garment worn by a patient.

Clause 7: The external medical device of any one of clauses 1-6, wherein the device can further comprise a garment worn about a torso of a patient.

Clause 8: The external medical device of any one of clauses 1-7, wherein the battery receptacle can be configured to receive a dumb battery.

Clause 9: The external medical device of any one of clauses 1-8, wherein the battery receptacle can be configured to receive a smart battery.

Clause 10: The external medical device of any one of clauses 1-9, wherein the smart battery can include a portion of the battery circuit.

Clause 11: The external medical device of any one of clauses 1-10, wherein the battery can be a rechargeable battery.

Clause 12: The external medical device of any one of clauses 1-11, wherein the device can further include a battery charging circuit operative for charging the battery.

Clause 13: The external medical device of any one of clauses 1-12, wherein the device can further comprise: one or more capacitors operative for storing charge; and a capacitor charging circuit operative for causing the battery to charge the one or more capacitors.

Clause 14: The external medical device of any one of clauses 1-13, wherein the capacitor charging circuit can comprise a voltage converter.

Clause 15: The external medical device of any one of clauses 1-14, wherein the battery circuit can comprise the capacitor charging circuit.

Clause 16: The external medical device of any one of clauses 1-15, wherein the battery circuit can be separate from the charging circuit.

Clause 17: The external medical device of any one of clauses 1-16, wherein the capacitor charging circuit can be periodically enabled to test charge the one or more capacitors.

Clause 18: The external medical device of any one of clauses 1-17, wherein monitoring the condition of the battery can comprise periodically enabling the capacitor charging circuit and determining an internal resistance of the battery based on a current drawn by the capacitor charging circuit from the battery.

Clause 19: The external medical device of any one of clauses 1-18, wherein monitoring a condition of the battery can comprise monitoring a battery voltage during a predetermined time period and determining an internal resistance of the battery based on the monitored battery voltage.

Clause 20: The external medical device of any one of clauses 1-19, wherein the predetermined time period can comprise a period of time for charging the capacitor.

Clause 21: The external medical device of any one of clauses 1-20, wherein the predetermined time period can be within 2-35 seconds.

Clause 22: The external medical device of any one of clauses 1-21, wherein the predetermined time period can be within 15-20 seconds.

Clause 23: The external medical device of any one of clauses 1-22, wherein determining the battery life status of the battery can comprise determining a remaining amount of battery life based on a predetermined tolerance of internal resistance values associated with the battery, wherein the predetermined tolerance is defined by the battery life threshold expressed as a predetermined maximum internal resistance threshold of the battery beyond which the battery must be replaced.

Clause 24: The external medical device of any one of clauses 1-23, wherein the predetermined tolerance of internal resistance values can be within a range of 0.01 to 0.6 ohms.

Clause 25: The external medical device of any one of clauses 1-24, wherein the predetermined tolerance of internal resistance values can be within a range of 0.1 to 0.7 ohms.

Clause 26: The external medical device of any one of clauses 1-25, wherein the predetermined maximum internal resistance threshold of the battery can be 0.9 ohms.

Clause 27: The external medical device of any one of clauses 1-26, wherein determining the battery life status of the battery can comprise determining whether the monitored condition is outside a predetermined tolerance.

Clause 28: The external medical device of any one of clauses 1-27, wherein causing the device to be operated in the low power operating mode can comprise causing an output device to output at least one of an audio, visual, and tactile alert in response to the determined battery life status.

Clause 29: The external medical device of any one of clauses 1-28, wherein the device can further comprise a communication device operative for causing the device to send a message concerning the battery life status to a remote server.

Clause 30: The external medical device of any one of clauses 1-29, wherein causing the device to be operated in the low power operating mode can comprise causing the device to perform predetermined critical device operations and turning off predetermined non-critical device operations.

Clause 31: The external medical device of any one of clauses 1-30, wherein the predetermined non-critical device operations can comprise one or more of data download; display backlight; data storage; running diagnostics; location determination; certain device self-tests; communications functionality; and/or testing of communications module.

Clause 32: The external medical device of any one of clauses 1-31, wherein causing the device to be operated in the low power operating mode can comprise causing the device to change a treatment sequence of the device.

Clause 33: The external medical device of any one of clauses 1-32, wherein causing the device to change the treatment sequence can comprise, as a first action of one or more actions, periodically enabling and disabling a charging circuit for charging one or more capacitors, and causing the device to perform a second action of the one or more actions during a period when the charging circuit is disabled.

Clause 34: The external medical device of any one of clauses 1-33, wherein changing the treatment sequence can include at least one of: suspending performance of at least one non-critical function; and suspending performance of at least one critical function during performance of the first action.

Clause 35: The external medical device of any one of clauses 1-34, wherein, the non-critical device functions can include, data download, display backlight, data storage, running diagnostics, location determination, certain device self-tests; communications functionality; and/or testing of communications module; and critical device functions can include, monitor patient physiological signals, treat (shock) patient with charge stored in the one or more capacitors, generate audio, visual, and/or tactile signals relating to treating a patient, bystander warning(s), and/or dispensing conductive gel.

Clause 36: The external medical device of any one of clauses 1-35, wherein the second action can comprise deploying a conductive gel on a surface of a treatment electrode.

Clause 37: In an example, a battery circuit for use with an external medical device, comprises: a battery receptacle configured to receive a battery that can support a plurality of charge-discharge cycles prior to a predetermined battery life threshold; and battery circuitry operative for: monitoring a condition of the battery; determining a battery life status of the battery based on the monitored condition and the predetermined battery life threshold; and responsive to the determined battery life status, causing a battery life status notification to be generated.

Clause 38: The battery circuit of clause 37, wherein the battery circuitry can be disposed in the external medical device.

Clause 39: The battery circuit of clauses 37 or 38, wherein the battery circuitry can be disposed in a unit that is separate and distinct from the external medical device.

Clause 40: The battery circuit of any one of clauses 37-39, wherein a portion of the battery circuitry can be disposed in the battery.

Clause 41: In an example, an external medical device comprises: a capacitor operative for storing a charge; a converter operative for charging the capacitor with electrical charge from a battery; circuitry operative for monitoring a battery voltage of the battery during charging of the capacitor by the converter and for determining an internal battery resistance based on the monitored battery voltage; and an output device, responsive to the internal battery resistance being out of tolerance, for outputting at least one signal.

Clause 42: The external medical device of clause 41, wherein the at least one signal can include at least one of the following: a visual signal; an audible signal; and a tactile signal.

Clause 43: The external medical device of clauses 41 or 42, wherein the internal battery resistance can be out of tolerance under at least one of the following conditions: the internal battery resistance exceeds a predetermined maximum internal resistance threshold value; and a trend of two or more internal battery resistances determined at different times is outside of a predetermined trend.

Clause 44: In an example, an external medical device comprises: a capacitor operative for storing a charge; a converter operative for charging the capacitor with electrical charge from a battery; and circuitry operative for monitoring a battery voltage of the battery during charging of the capacitor by the converter and for determining an internal battery resistance based on the monitored battery voltage, wherein: the circuitry is responsive to the internal battery resistance being within tolerance for performing a first set of device functions; and the circuitry is responsive to the internal battery resistance being out of tolerance for performing a second set of device functions that is a subset of the first set of device functions that is less than the first set of device functions.

Clause 45: The external medical device of clause 44, wherein: the first set of device functions can include critical and non-critical device functions; and the second set of device functions can include critical device functions only.

Clause 46: The external medical device of clauses 44 or 45, wherein the critical device functions can include one or more of the following: monitoring a physiological signal of the patient, treating the patient with charge stored in the capacitor, generating one or more of an audio, visual and/or tactile signal, bystander warning(s), and causing a conductive gel to dispense onto a patient.

Clause 47: The external medical device of any one of clauses 44-46, wherein non-critical functions can include one or more of the following: data download, display backlight, data storage, running diagnostics, location determination, certain device self-tests; communications functionality; and/or testing of communications module.

Clause 48: In an example, an external medical device comprises: a capacitor operative for storing electrical charge; a converter operative for charging the capacitor with electrical charge from a battery; and circuitry operative for monitoring a battery voltage of the battery during charging of the capacitor by the converter and for determining an internal battery resistance based on the monitored battery voltage, wherein, during a charging cycle of the capacitor, the converter is responsive to the internal battery resistance being within tolerance for charging the capacitor with electrical charge from the battery in a first charging manner; and the converter is responsive to the internal battery resistance being out of tolerance for charging the capacitor with electrical charge from the battery in a second charging manner.

Clause 49: The external medical device of clause 48, wherein: the first charging manner can include the converter continuously charging the capacitor with electrical charge from the battery during the charging cycle; and the second charging manner can include the converter charging the capacitor with electrical charge from the battery in two or more charging steps during the charging cycle.

Clause 50: The external medical device of clauses 48 or 49, wherein the two or more charging steps can have different duty cycles.

Clause 51: The external medical device of any one of clauses 48-50, wherein the second charging manner can include a pause in charging between at least one pair of charging steps during the charging cycle.

Clause 52: The external medical device of any one of clauses 48-51, wherein the converter can be a DC-DC converter.

Clause 53: In an example, an external medical device comprises: a capacitor operative for storing a charge; a converter operative for charging the capacitor with electrical charge from either a main, rechargeable battery or a backup battery; and circuitry operative for monitoring a battery voltage of the main, rechargeable battery during charging of the capacitor from the main, rechargeable battery and, in response to determining that an internal battery resistance of the main, rechargeable battery is out of tolerance based on the monitored battery voltage, for causing the converter to charge the capacitor from the backup battery.

Clause 54: The external medical device of clause 53, wherein the circuitry can be further operative for determining when the converter is coupled to a replacement main, rechargeable battery having an internal battery resistance that is within tolerance and for reverting to charging the capacitor from the main, replacement rechargeable battery from the backup battery.

Clause 55: The external medical device of clauses 53 or 54, wherein the internal battery resistance can be out of tolerance under at least one of the following conditions: the internal battery resistance exceeds a predetermined maximum internal resistance threshold value; and a trend of two or more internal battery resistances determined at different times is outside of a predetermined trend.

Clause 56: The external medical device of any one of clauses 53-55, wherein the backup battery can be operative for charging the capacitor at 2.5 amps for up to 30 seconds.

Clause 57: The external medical device of any one of clauses 53-56, wherein the backup battery can be a lithium-ion battery.

Clause 58: In an example, an external medical device comprises: a capacitor operative for storing electrical charge; a converter operative for charging the capacitor with electrical charge from a battery; and circuitry operative for monitoring a battery voltage of the battery during charging of the capacitor by the converter and, in response to determining that an internal battery resistance is out of tolerance based on the monitored battery voltage, for isolating the capacitor from a component, subsystem, or system of the device that drains the charge stored in the capacitor when the capacitor is not being used to treat a patient with the charge stored in the capacitor.

Clause 59: The external medical device of clause 58, wherein the capacitor can be a double-layer capacitor or a lithium-ion capacitor.

Clause 60: In an example, an external medical device comprises: a capacitor operative for storing electrical charge; a converter operative for charging the capacitor with electrical charge from a battery that also supplies electrical power to a component, subsystem, or system of the device; and circuitry operative for monitoring a battery voltage of the battery during charging of the capacitor by the converter and, in response to determining that an internal battery resistance is out of tolerance based on the monitored battery voltage, for causing the component, subsystem or system of the device to revert from receiving power from the battery to receiving power from the capacitor.

Advantages of the above-described ambulatory medical devices include increased reliability, less susceptibility to critical failures, and enhanced management of battery power when the battery is approaching its end-of-life (EOL).

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which:

FIG. 8 is a chart of internal resistances of the batteries of the battery pack shown in FIG. 4 determined at different times;

DETAILED DESCRIPTION

Figure 1:
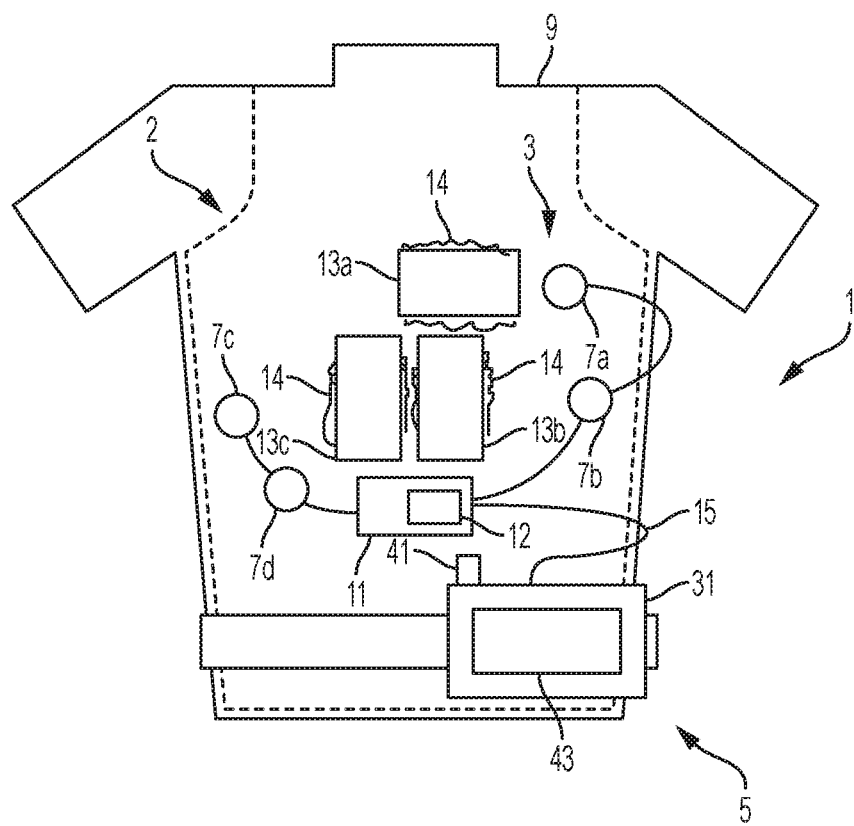
FIG. 1 is a schematic drawing of an external medical device.

As used herein, the singular form of "a", "an", and "the" include plural reference unless the context clearly dictates otherwise.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

Unless indicated to the contrary, the numerical parameters set forth in the following specification and attached claims are approximations that can vary depending upon the desired properties sought to be obtained by the present disclosure. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

This disclosure relates to battery management components, modules, subsystems, circuitry, and/or techniques for use in medical devices. For example, such battery management components, modules, subsystems, circuitry, and/or techniques can be used in the context of implanted or external medical devices for monitoring and/or providing treatment to a patient. For example, such medical devices can include monitoring devices configured to monitor a patient for certain medical conditions. In some implementations, such devices are capable of, in addition to monitoring for medical conditions, providing treatment to a patient based on detecting a predetermined medical condition.

The devices as described herein may be capable of continuously, substantially continuously, long-term, and/or extended use or wear by, or attachment or connection to a patient.

For example, devices as described herein may be capable of being used or worn by, or attached or connected to a patient, without substantial interruption for a predetermined period of time. In some examples, such devices may be capable of being used or worn by, or attached or connected to a patient for example, up to hours or beyond (e.g., weeks, months, or even years).

In some implementations, such devices may be removed for a period of time before use, wear, attachment, or connection to the patient is resumed, e.g., to change batteries, to change the garment, and/or to take a shower, without departing from the scope of the examples described herein.

The devices as described herein may be capable of continuously, substantially continuously, long-term and/or extended monitoring of a patient.

For example, devices as described herein may be capable of providing cardiac monitoring without substantial interruption for a predetermined period of time. In some examples, such devices may be capable of continuously or substantially continuously monitoring a patient for cardiac-related information (e.g., electrocardiogram (ECG) information, including arrhythmia information, heart sounds, etc.) and/or non-cardiac information (e.g., blood oxygen, the patient's temperature, glucose levels, and/or lung sounds), for example, up to hours or beyond (e.g., weeks, months, or even years).

In some implementations, such devices may be powered down for a period of time before monitoring is resumed, e.g., to change batteries, to change the garment, and/or to take a shower, without departing from the scope of the examples described herein.

In some instances, the devices may carry out its monitoring in periodic or aperiodic time intervals or times. For example, the monitoring during intervals or times can be triggered by a user action or another event. For example, one or more durations between the periodic or aperiodic intervals or times can be user-configurable.

In various implementations, the devices may be operated on battery power for a duration of the device's use after which the batteries may be replaced and/or recharged. For example, external medical devices as disclosed herein can include cardiac monitoring and/or automated pacing devices or defibrillators, such as in-facility monitoring defibrillators (e.g., for patients that are confined to a limited space within a facility, such as within a hospital environment, to a patient's room) or outpatient wearable defibrillators. Such devices can be configured to monitor a patient for an arrhythmia condition such as bradycardia, ventricular tachycardia (VT), or ventricular fibrillation (VF). In addition, while the detection methods and systems described hereinafter are disclosed as detecting VT and VF, this is not to be construed as limiting the invention as other arrhythmias, such as, but not limited to, atrial arrhythmias such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventrical arrhythmias such as premature ventricular contractions (PVCs) and accelerated idioventricular rhythm, may also be detected. In the case of treatment devices, such as pacing and/or defibrillating devices, if an arrhythmia condition is detected, the device can automatically provide a pacing or defibrillation pulse or shock to treat the condition.

As noted, medical devices as disclosed herein can include wearable cardiac monitors and/or defibrillators (which can include pacing functionality). In some examples, medical devices as disclosed herein can include implanted medical devices (e.g., implantable defibrillators or pacing devices). Devices described herein as external or non-invasive can be contrasted with invasive medical devices, such as implantable defibrillators or implantable pacing devices.

Other example external devices capable of employing the battery management systems and/or techniques described herein include automated cardiac monitors, and/or defibrillators for use in certain specialized conditions and/or environments, such as in combat zones or within emergency vehicles. For example, such devices may be portable and configured so that they can be used immediately (or substantially immediately) in a life-saving emergency. In some examples, the automated defibrillators described herein can be pacing-enabled, e.g., capable of providing therapeutic pacing pulses to the patient. In an example, the external medical devices as described herein can be ambulatory, e.g., the device is capable of and designed for moving with the patient.

In an example, the medical device can include circuitry for managing the battery life of a device battery. In various implementations, the battery life status of a battery can indicate a remaining operational life of the battery such that, once the operational life is exhausted, as indicated, for example, when the battery life status reaches or transgresses a predetermined battery life threshold value, the battery should be replaced. The predetermined battery life threshold value as described herein depends on a nature of an underlying battery condition selected as a basis for monitoring and/or recording the battery life status. For example, the battery condition can be characterized through one or more battery parameters and/or combination of such parameters as described below. For example, in the case of batteries that can undergo multiple charge-discharge cycles during operational life (e.g., rechargeable Li-Ion batteries), the battery life status can reflect a status of one or more underlying battery parameters, such as an internal resistance of the battery, and/or an amount of time, and/or a number of charge-discharge cycles remaining before the battery, even after being charged, is unable to (or deemed unable to) provide required power for the medical device to perform certain functions. In another example, the battery life status can reflect an amount of time or a number of charge-discharge cycles since the battery was first put in use. In an example, the battery life status can be provided in terms of an elapsed or a remaining number of ampere-hours. In some examples, the battery life status can reflect a function based on one or more of the above battery parameters, such as, an internal resistance of the battery, and/or an amount of time, and/ or a number of charge-discharge cycles remaining before the battery, even after being charged, is unable to (or deemed unable to) provide required power for the medical device to perform certain functions, an amount of time or a number of charge-discharge cycles since the battery was first put in use, and/or an elapsed or a remaining number of ampere-hours. It should be appreciated that the battery parameters considered in evaluating the battery life status may not be limited to the examples above, but may include any of other known battery parameters suited for the purpose.

In an example, exhaustion of operational battery life such that the battery, even after being charged, is unable to (or deemed unable to) provide the required power, may be referred to as end-of-life (EOL). Various arrangements of battery circuits can be employed to monitor the battery life status of a battery as well as the battery's use.

For example, a battery circuit can be configured to directly or indirectly calculate or estimate the internal resistance of the battery in a dynamic fashion. Increasing internal resistance indicates that a rechargeable battery may be approaching the end-of-life (EOL). Thus, a change in internal resistance may be used as an indicator of battery life status. For example, as noted below, a certain internal resistance value can be selected as a predetermined battery life threshold value. Such a value can be based on experimental determinations of EOL, or be selected to be within a predetermined range, or within a predetermined range of percentage points of the experimentally determined EOL.

When internal resistance reaches or exceeds the predetermined threshold value, it can be determined that the battery has reached its EOL and should be replaced. In this regard, the battery life status can be specified by indicating a current internal resistance of the battery or in terms of a remaining range of internal resistance values.

For example, the EOL may be specified through a user-provided parameter stored in a memory component of the circuit indicating the predetermined battery life threshold. In an example, the EOL can be specified based on an in-service configuration process before the medical device containing the battery is deployed in the field. In another example, the EOL can be determined by statistically observing a sample of similar batteries (e.g., Li-Ion batteries having a same or similar set of operating parameters). In this regard, the EOL is selected based on an observed value of, e.g., internal resistance of the battery at or beyond which the battery is unable to (or deemed unable to) provide the required power to sustain one or more operations of the medical devices. Accordingly, the predetermined battery life threshold may be specified in terms of a predetermined maximum internal resistance value beyond which the battery should be replaced (e.g., the operational life of the battery has been exhausted such that even after being charged, the battery is no longer able to provide the required power). For example, the predetermined maximum internal resistance value (which corresponds to the battery life threshold) may be set to a value between about 0.8-0.9 ohms (e.g., 0.9 ohms).

Example Medical Device:

In an example and with reference to FIG. 1, the external medical device can be configured as a wearable defibrillator 1, such as the LifeVest® wearable defibrillator available from ZOLL® Medical Corporation of Pittsburgh, Pa. and Chelmsford, Mass. The wearable defibrillator 1 can be worn by a patient 9 and can include a garment 2 (shown in phantom in FIG. 1), an electrode assembly 3, and a monitor 5 operatively connected to the electrode assembly 3. The garment 2 can be configured as a harness, shirt, or other apparel and is configured to permit the defibrillator 1 to be worn on about the torso of the patient 9. The electrode assembly 3 can be configured to be assembled within the garment 2.

Such wearable defibrillators may be configured for long term or extended wear. For example, the wearable defibrillator may be continuously or substantially continuously worn by a patient for two to three months at a time. During the period of time in which they are worn by the patient, the wearable defibrillator 1 can be configured to continuously or substantially continuously monitor the vital signs of the patient, to be user-friendly and accessible, to be as light-weight, comfortable, and portable as possible, and to be capable of delivering one or more life-saving therapeutic shocks when needed. Non-limiting examples of suitable wearable defibrillators are disclosed in U.S. Pat. Nos. 4,928,690; 5,078,134; 5,741,306; 5,944,669; 6,065,154; 6,253,099; 6,280,461; 6,681,003; 8,271,082; and 8,369,944, the entirety of all of which are incorporated by reference herein.

With continued reference to FIG. 1, the electrode assembly 3 includes a plurality of electrodes, such as electrodes 7a, 7b, 7c, and 7d, which contact a patient 9 when the wearable defibrillator 1 is worn by the patient 9. According to one example, the electrodes 7a, 7b, 7c, and 7d are configured to receive ECG signals from the patient 9. For instance, the electrodes 7a, 7b, 7c, and 7d can be positioned on the patient 9 to receive ECG signals from a front-to-back channel and from a side-to-side channel. For example, the front-to-back (FB) channel can include one of electrodes 7a, 7b, 7c, and 7d positioned on the chest of the patient 9 and another one of the electrodes 7a, 7b, 7c, and 7d positioned on the back of the patient 9. For example, the side-to-side (SS) channel includes one of the electrodes 7a, 7b, 7c, and 7d positioned on the left side of the chest and another one of the electrodes 7a, 7b, 7c, and 7d positioned on the right side of the chest of the patient 9. In some examples, the electrodes 7a, 7b, 7c, and 7d can be operatively connected to a distribution node 11 of the electrode assembly 3.

In some implementations, the electrode assembly 3 can also comprise therapy pads 13a, 13b, and 13c operatively connected to the distribution node 11. The therapy pads 13a, 13b, and 13c can be configured to deliver one or more life-saving therapeutic shocks when needed. In some examples, the electrode assembly 3 can also include other sensing electrodes and devices (not shown) such as, but not limited to, heart beat sensors, accelerometers, and sensors capable of measuring blood pressure, heart rate, thoracic impedance, respiration rate, heart sounds, acoustic sensors, audio transducers, and the activity level of the subject. The electrode assembly 3 can further comprise a tactile stimulator 12, such as a vibrator, positioned within the distribution node 11 to provide tactile stimulation to the patient 9 as described in greater detail hereinafter.

The monitor 5 can be operatively connected to one or more of the therapy pads 13a, 13b, and 13c and electrodes 7a, 7b, 7c, and 7d via a trunk cable 15 or any other suitable cable or connection device. Wiring or other connection devices can be used to connect at least one portion of the distribution node 11 to the electrodes 7a, 7b, 7c, and 7d and therapy pads 13a, 13b, and 13c. Alternatively, the monitor 5 can be operatively connected to one or more of the electrodes 7a, 7b, 7c, and 7d, therapy pads 13a, 13b, and 13c, and distribution node 11 by a wireless connection or a combination of wireless and wired connections.

The distribution node 11 is configured to obtain ECG data from the electrodes 7a, 7b, 7c, and 7d, digitize this data, and transfer this data to the monitor 5. Accordingly, the distribution node 11 includes a processor, such as a belt node processor (BNP) 17 (see FIGS. 3A and 4), operatively connected to electrodes 7a, 7b, 7c, and 7d and configured to receive signals representing the ECG of the patient 9 from the electrodes 7a, 7b, 7c, and 7d. The BNP 17 communicates with the monitor 5 via a Controller Area Network (CAN) bus 19 (see FIG. 4) or any other suitable bus that comprises trunk cable 15. The BNP 17 is also configured to sense whether one or more of electrodes 7a, 7b, 7c, and 7d have fallen off the patient's body, to control the tactile stimulator 12, and to fire the electrode gel interface for providing electrolytic gel 14 (FIG. 1) to the therapy pads 13a, 13b, and 13c when a request is received from the monitor 5.

Figure 2:
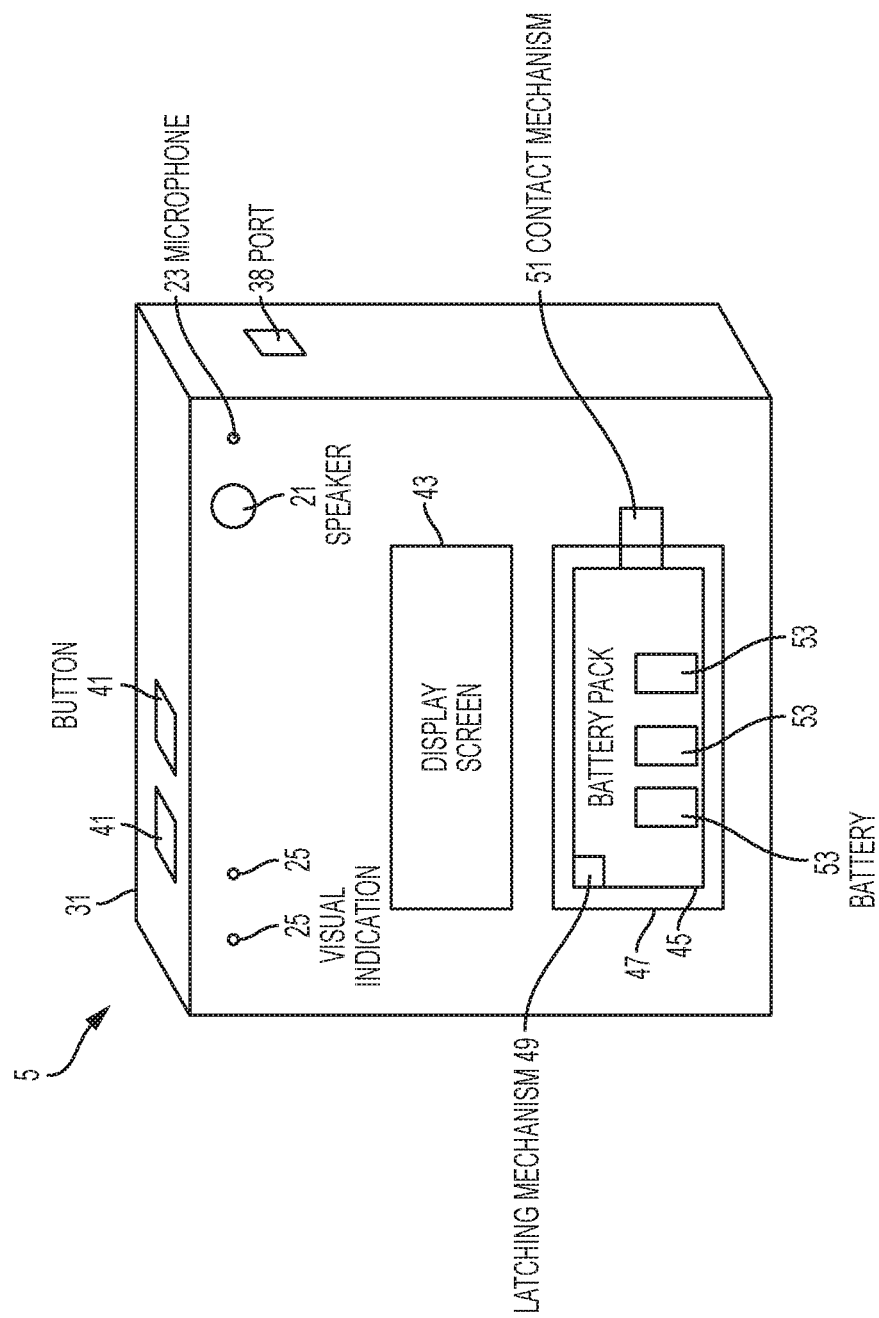
FIG. 2 is a block diagram of an example monitor for an external medical device.

With reference to FIG. 2, and with continuing reference to FIG. 1, the monitor 5 can include an external housing 31 having a port 38 to which the ECG electrodes 7a, 7b, 7c, and 7d and therapy pads 13a, 13b, and 13c of the electrode assembly 3 are operatively coupled to the monitor 5 via the trunk cable 15. The external housing 31 further comprises at least one, and for example, a pair of patient response buttons 41 positioned, for example, in the top left corner of the housing 31. The external housing 31 of the monitor 5 can also include a display screen 43 for providing information to the patient 9 and for providing a user input device to the patient 9. In other embodiments, visual indicators 25, such as LED bulbs, can be positioned on the housing 31 for providing information to the patient 9. The external housing 31 can include an audio system having a speaker 21 and a microphone 23 positioned on the external housing 31. The speaker 21 is desirably positioned at least 2.5 inches away from the microphone 23 to minimize feedback. As will be discussed herein, the display screen 43, visual indicators 25, and speaker 21 can be used for providing feedback and/or alerts to the patient 9.

In an example, the external housing 31 of the monitor 5 can comprise a rechargeable and removable battery pack 45 positioned within a battery receptacle 47 provided in the external housing 31. In some cases, two battery packs 45 can be supplied to a patient to provide substantially uninterrupted device use while one battery pack 45 is charging. The battery pack 45 is secured within battery receptacle 47 by a battery latching mechanism 49. The battery latching mechanism 49 is positioned at the top left corner of the battery pack 45 to allow for the battery pack 45 to be removed from the external housing 31. The battery receptacle 47 includes a contact mechanism 51 configured to engage a corresponding contact mechanism (not shown) extending from the battery pack 45. Electrical current can be transferred between the battery pack 45 and monitor 5 through the corresponding contact mechanisms 51 for providing power to the monitor 5 and/or for charging the battery pack 45.

The battery pack 45 can house one or more rechargeable batteries or cells 53, which provide power to the monitor 5 and/or wearable defibrillator 1. For example, the battery pack 45 can consist of an enclosure (e.g., a plastic enclosure) containing three or more Lithium-Ion cells 53. Contacts are mounted on the enclosure to connect the battery pack 45 to the monitor 5 or the battery charger for charging as described in further detail herein.

In some examples, the batteries or cells 53 may be disposed within a receptacle to allow a user to replace the battery. For instance, a mechanism may be provided to allow the user to release the battery from the receptacle. In some examples, the batteries or cells 53 may be disposed within the housing 31 of the monitor 5 in such a manner that the user is unable to remove/replace the battery (e.g., the battery receptacle 47 is sealed and inaccessible to the user).

In some implementations, the battery pack 45 can be a "smart" battery pack and include circuitry to monitor the charge and discharge current and store a capacity value for use by the monitor. In an example, when fully charged, the batteries 53 of battery pack 45 can provide power to monitor the patient 9 for at least 24 hours at an ambient temperature of 20° C. (with the patient wearing the device), with sufficient reserve single charge-cycle capacity to deliver at least one 5-pulse defibrillating sequence at a maximum energy setting (150 joules) (e.g., −5%/+5% to into a 50 ohm load). In an example, the batteries 53 of battery pack 45 can also provide sufficient single charge-cycle capacity to support full energy pacing for 60 minutes at the end of a 24 hour monitoring period. For example, the batteries 53 of battery pack 45 can have sufficient single charge-cycle capacity to allow the wearable defibrillator 1 to administer one or more therapeutic shocks as well as provide power to all of the internal components of the defibrillator 1. For example, the battery pack can include three or more 18 mm×65 mm, 1,800 (or more) milliampere-hour Li-Ion rechargeable battery cells.

Further details of the monitor 5 can be found in U.S. patent application Ser. No. 14/448,997, which is hereby incorporated by reference in its entirety.

In some implementations, the medical device as described herein can be a hospital-based wearable defibrillator and/or pacing device. For example, such a hospital-based device can include a defibrillator and/or pacing device configured for continuous or substantially continuous use, wear, connection, attachment, or monitoring to/of a patient in a hospital environment (e.g., on an in-patient basis). The hospital-based device can include a plurality of therapy and sensing electrodes that are attached to the patient's skin. In some examples, the electrodes are disposable adhesive electrodes. In some implementations, the electrodes are affixed to an electrode assembly (a patch), which can then be adhesively attached to the patient's skin. The electrodes can be attached to the patient's skin at particular locations as prescribed by a trained professional.

In operation, the hospital-based device can include a monitor configured to operate in a manner that is different from that of the monitor of wearable defibrillator 1 described above with respect to FIG. 1. As described in more detail herein, an interface, prompts, and communication performed by the hospital-based device can be configured for and/or directed to a user other than the patient 9, e.g., a caregiver, such as a nurse or a patient service representative. For example, a caregiver can program the device and/or set the device up for use by the patient 9. The interface, prompts, and communication can be directed to the patient 9 in scenarios, such as when a response is required to let the device know whether or not the patient 9 is conscious, which can be used in deciding when to shock the patient 9, and when a patient is given an alert to call the caregiver.

In some implementations, the medical device as described herein can be configured to monitor a patient presenting with syncope (e.g., by analyzing the patient's cardiac activity for aberrant patterns that can indicate abnormal physiological function). In some examples, aberrant patterns may occur prior to, during, or after the onset of syncope symptoms. For example, the defibrillator can include a plurality of electrodes and/or an electrode assembly (patch) that can be adhesively attached to the patient's skin. The patient may replace the electrodes and/or patches as prescribed. The electrodes can be positioned in a configuration similar to that of the hospital-based device described above.

System Architecture of an Example Medical Device

Figure 3A:
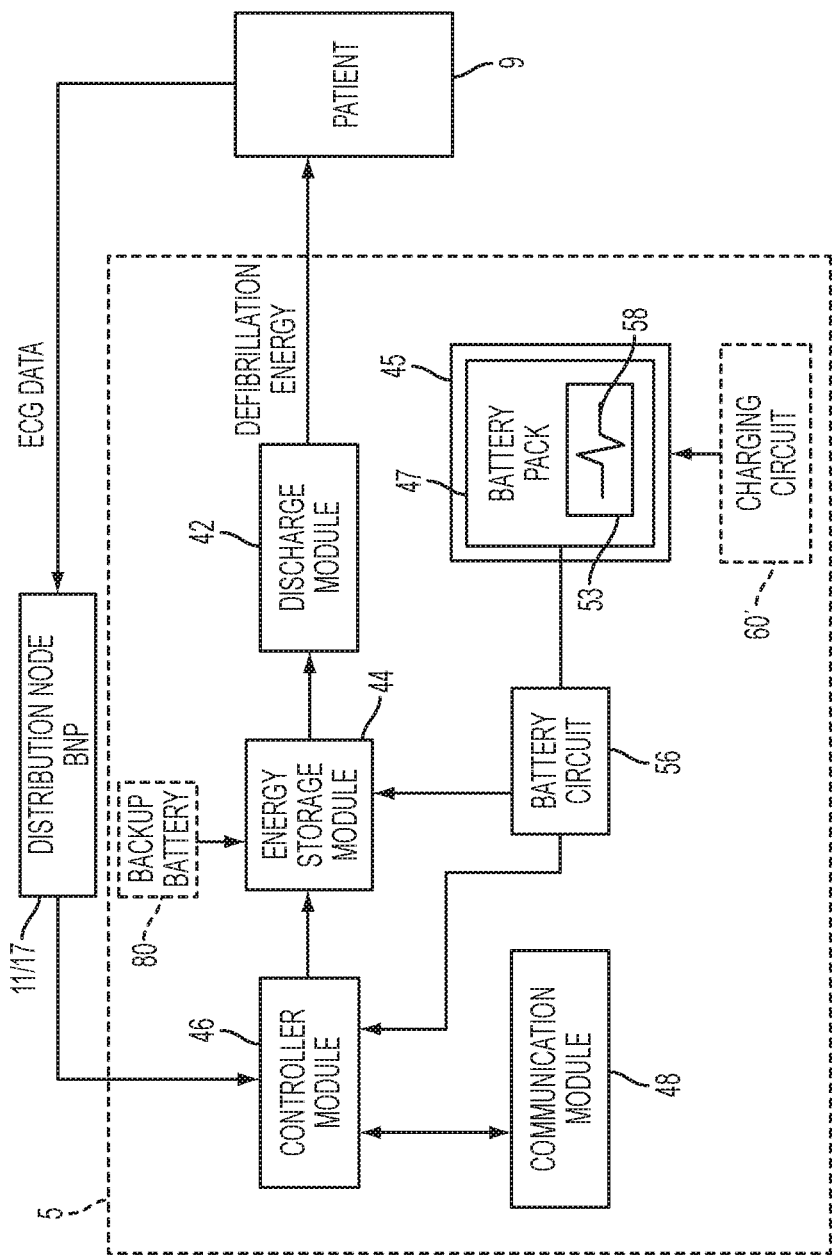
FIG. 3A is an example block diagram illustrating the manner in which functional components of the external medical device can interact.

With reference to FIG. 3A and with continuing reference to FIGS. 1 and 2, the functional components of the monitor 5 can be provided within the external housing 31 of the monitor 5. In one example, the functional components of monitor 5 can be provided on a distributed printed circuit board as disclosed in U.S. patent application Ser. No. 14/448,857, which is hereby incorporated by reference in its entirety. In one example, the functional components of monitor 5 can comprise a discharge module 42, an energy storage module 44, a controller 46, and a communication module 48. The discharge module 42 is for selectively delivering an energy pulse to the patient 9 via therapy electrodes 13a, 13b, and 13c. The energy storage module 44 can be operatively connected to the discharge module 42. The controller 46 can be operatively connected to the energy storage module 44 and can be configured to control the delivery of the energy pulse to the patient 9. The communication module 48 can be operatively connected to the controller 46.

Figure 4:
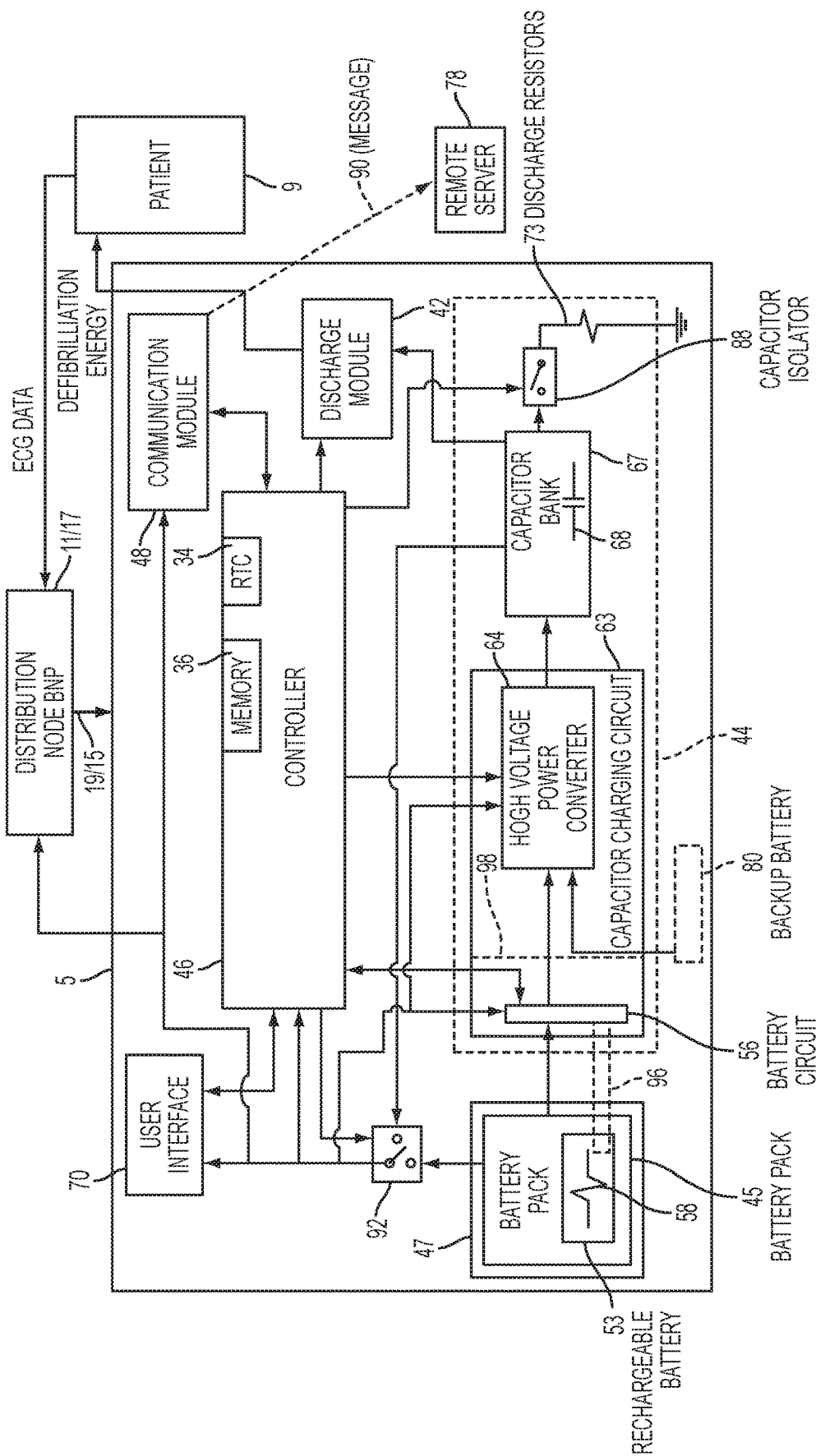
FIG. 4 is an example schematic diagram of an external medical device.

In one example, the energy storage module 44 can include a high voltage power converter 64 (shown in FIG. 4) and a capacitive device, such as a bank of capacitors 67 (shown in FIG. 4). The discharge module 42 can include at least one high-voltage switch and can be configured to selectively deliver an energy pulse stored in the energy storage module 44 to the patient 9 based on a signal from controller 46. The energy pulse is sent from the discharge module 42 through the port 38 to the patient 9 via therapy pads 13a, 13b, and 13c.

A biphasic waveform can be delivered to the patient 9 by switching the at least one high voltage switch of the discharge module 42. The operation of the pulse delivery system can be dynamic and depend on the patient's body impedance while the pulse is being delivered. For example, an amount of energy delivered can be held constant while varying the duration of the first phase and the second phase. In another example, a monophasic waveform can be delivered to the patient depending on the patient's condition or a condition of energy storage module 44.

Figure 3B:
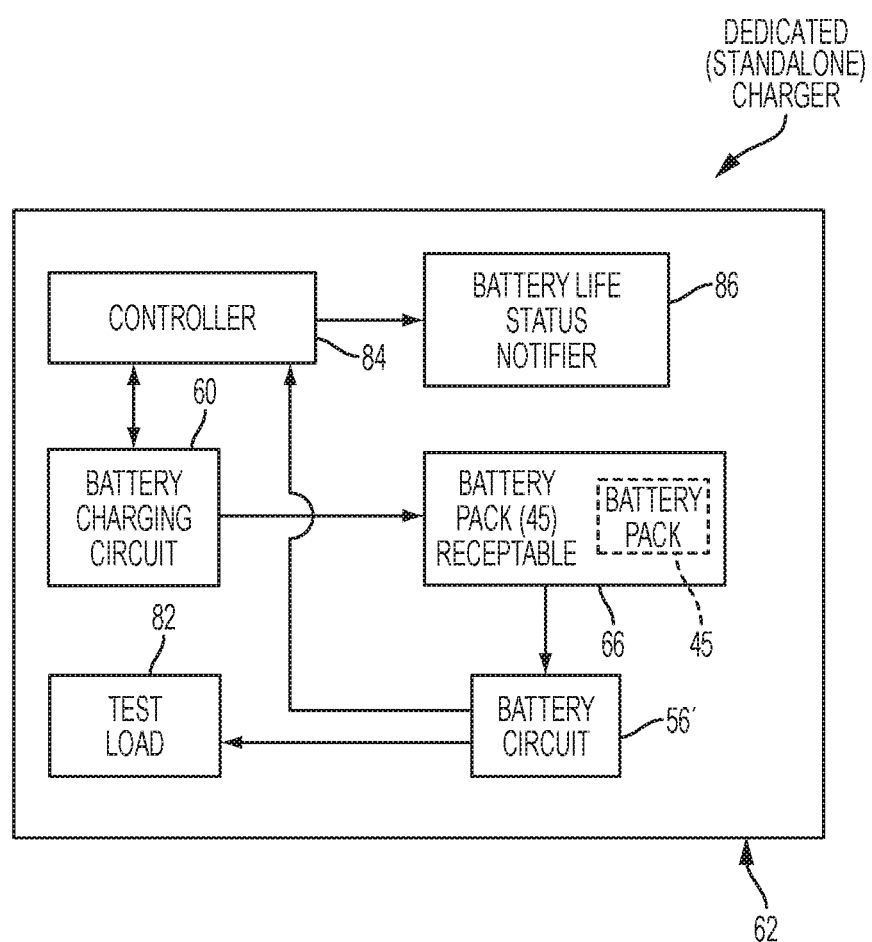
FIG. 3B is an example block diagram of a dedicated, standalone charger that can be used to charge the battery pack of the monitor shown in FIG. 2 upon removal of the battery pack from the monitor.

FIG. 3B is a block diagram of a dedicated, standalone charger 62 that can be used for charging battery pack 45 upon removal of battery pack 45 from monitor 5. Dedicated, standalone charger 62 will be described in greater detail hereinafter.

With reference to FIG. 4, and with continuing reference to FIGS. 1-3B, controller 46 can include one or more processors, each of which operates under the control of a control program that executes at runtime for performing certain functions of the medical device, e.g., wearable defibrillator 1.

Also, or alternatively to the one or more processors, controller 46 can include discrete and/or integrated electrical and/or electronic circuitry that is configured to perform the functions described herein (either alone or in combination with one or more processors), with or without a control program. In an example, the electrical and/or electronic circuitry of controller 46 can include one or more discrete elements, such as, without limitation, one or more of the following discrete elements: transistor, resistor, capacitor, inductor, memristor, diode, loudspeaker, buzzer, linear variable differential transformer (LVDT), rotary encoder, shaft encoder, inclinometer, motion sensor, vibration sensor, flow meter, strain gauge, accelerometer, thermocouple, thermopile, thermistor, resistance temperature detector (RTD), bolometer, thermal cutoff, magnetometer, gauss meter, hygrometer, photo resistor, LED or other light emitting device, and/or antenna.

In another example, the electrical and/or electronic circuitry of controller 46 can also or alternatively include one or more integrated circuits, such as, without limitation, analog integrated circuit, digital integrated circuit, mixed signal (analog and digital) integrated circuit, application specific integrated circuit (ASIC), programmable logic device (PLD), gate array, field programmable gate array (FPGA), and/or microelectromechanical systems (MEMS). In an example, these one or more integrated circuits can include one or more of analog-to-digital converter (ADC), a multiplexer, a power regulator, or some combination thereof.

In another example, controller 46 is operatively connected to a user interface 70 (comprised of one or more response buttons 41, speaker 21, one or more visual indicators 25, and/or display screen 43), the high voltage power converter 64, and the discharge module 42. Such configuration allows controller 46 to provide output to a patient 9, for example, through the display screen 43 and/or speaker 21, and accept input from the patient 9, for example, from response buttons 41 and/or display screen 43 when configured as a touch screen, as well as provide instructions to the high voltage power converter 64 and/or the discharge module 42 to deliver a therapeutic shock to the patient 9. For example, controller 46 can be used to provide certain functions within the wearable defibrillator 1, such as, but not limited to: high voltage converter control; discharge module control; real time clock (RTC) 34 (Date/time) for the system; execution of timing-critical software or functions, such as therapy pulse synchronization (e.g., synchronizing the pulse delivery to avoid delivering a pulse on a T wave); ECG acquisition from the CAN bus 19; ECG monitoring and arrhythmia detection; user interface control; treatment sequencing; audio message generation; and data communications and storage. An example of the methods used to detect abnormal heart rhythms can be found in U.S. Pat. No. 5,944,669, which is assigned to the assignee of the present application and which is hereby incorporated by reference in its entirety.

In some implementations, the BNP 17 can be operatively connected to the controller 46. The BNP 17 can act as an ECG data acquisition engine for the controller 46 via the CAN bus 19 as described hereinabove.

In an example, the communication module 48 can be controlled by controller 46 and can provide one or more communication devices for communicating information to and from the monitor 5. For example, the communication module 48 can include one or more communication devices, such as, without limitation, a GPS transceiver, a Bluetooth transceiver, a Wi-Fi modem, and/or a cellular modem. The communication module 48 is configured to communicate with a remote server 78 via one or more communication devices, e.g., the cellular modem. Alternatively, if the communication capabilities of one of the communication devices is not available (e.g., the cellular communications capabilities), the communication module 48 can communicate with the remote server 78 via another communication device, e.g., the Wi-Fi modem.

Monitor 5 includes additional elements that will be described in greater detail hereinafter.

For the purpose of simplicity, hereinafter the invention will be described with reference to monitor 5 shown in FIGS. 1, 3A, and 4 that includes controller 46. However, this is not to be construed as limiting the invention since it is envisioned that controller 46 can include any suitable and/or desirable combination of processor(s) and/or circuitry.

Operation of the Example Medical Device

Figure 5:
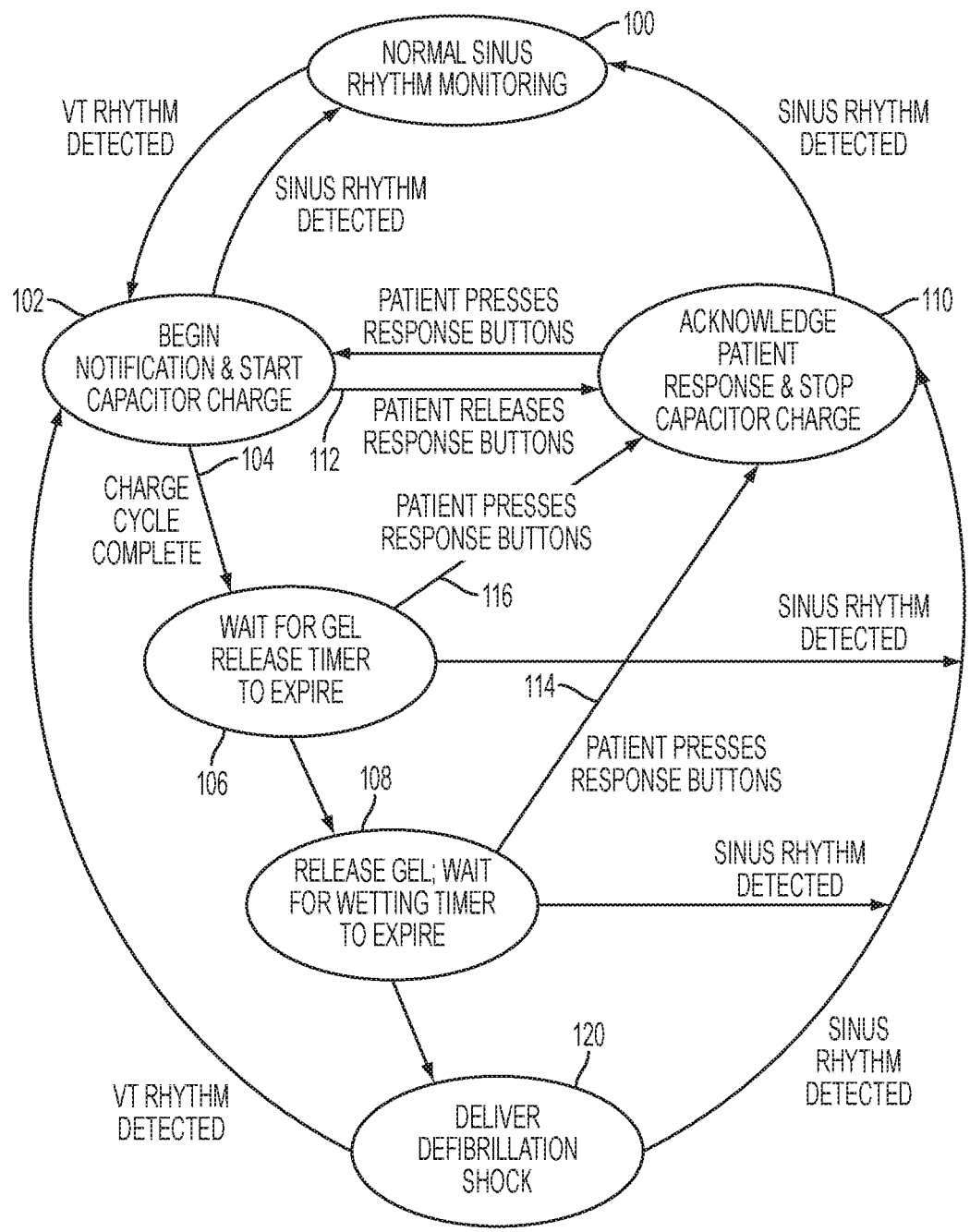
FIG. 5 is a state diagram illustrating operation of an external medical device.

With reference to FIG. 5, a description of the manner in which the monitor 5 operates when an abnormal event is detected by a detection algorithm of controller 46 will be described. Initially, controller 46 runs the detection algorithm and detecting normal sinus rhythm at 100. When the detection algorithm detects a VT or VF rhythm type, it dispatches an event to the state machine that is run on controller 46. The state machine exits the Normal Sinus Rhythm Monitoring state 100 when the event is received and transitions to a notification state 102 that begins the patient notification sequence to provide stimuli to the patient to make the patient aware that an event has been detected and starts a capacitor charge cycle. After the capacitors are fully charged a Charge Cycle Complete event 104 can be generated. As shown in FIG. 5, a timer can be used to determine when to release the gel 14 (see 106) and allow timing of a gel wetting period (see 108) to reduce transthoracic impedance.

At any point after the notification state 102, the patient can cancel the treatment sequence by pressing the response buttons 41 and the system acknowledges the patient response and stops charging capacitors 110. This is shown by arrows 112, 114, and 116. If the patient does not respond to the alarms and the timer for gel wetting expires, the state machine issues a command 120 for controller 46 to fire the defibrillator and treat the patient. Controller 46 continuously monitors the patient's rhythm and can detect a sinus rhythm if the defibrillation was successful and send an event notification to the state machine.

While the external medical device described herein is, in an example, a wearable medical device, this is not to be construed as limiting the invention. For example, it is envisioned that the battery life status monitoring described herein can be performed on or by any type of external medical device, including, without limitation, patient monitors, e.g., such as cardiac monitors used in mobile cardiac telemetry (MCT) and continuous event monitoring (CEM) scenarios, or automated external defibrillators that, in place of a garment 2, use electrodes or electrode assemblies (e.g., patches) that are affixed to a patient by, for example, adhesive. Further, the techniques and/or systems described herein can be applied in any other type of external medical device, e.g., external medical devices that rely upon a battery to supply, in addition to a few milliwatts or watts of power during normal operation, to provide tens or hundreds of watts upon demand when required for treatment of a patient.

Battery Life Status Monitoring—Low Power Operating Mode

With reference to FIGS. 3A-3B and 4, in an example, to facilitate detecting when the batteries 53 of battery pack 45 are reaching EOL, a battery circuit 56 can be operatively connected between battery receptacle 47, housing battery pack 45, and converter 64. Battery circuit 56 can be operative for monitoring a condition of one or more batteries 53 of battery pack 45.

In an example, battery circuit 56 monitors the condition of the one or more batteries 53 during a time when converter 64 is charging one or more capacitors 68 of capacitor bank 67. For example, the medical device can be configured to periodically (e.g., once a week) or aperiodically (occasionally) turn on the converter 64 (e.g., through a signal from controller 46) and test charge the capacitors 68, e.g., in order to test charging circuit operational integrity. The capacitors 68 can be subsequently discharged through an energy dissipating element 73 (for example, one or more discharge resistors or any component, system, or subsystem of monitor 5 that can drain charge stored in the one or more capacitors 68 when not being used to treat a patient with charge stored in the one or more capacitors 68) via a capacitor isolator 88 that is under the control of controller 46. During the process of test charging the capacitors 68, the controller 46 can cause the internal resistance of the battery to be calculated in a manner described below. The calculated value can be stored in memory, for example, such that a list of such values can be read out at a later time to study trends in battery life (see, e.g., FIG. 8 for a sample list of weekly internal resistance values).

In one example, battery circuit 56 monitors the output voltage of battery pack 45 when converter 64 is charging capacitors 68 of capacitor bank 67 and supplies a representation of this monitored voltage to controller 46. For example, the battery circuit 56 can store a delta voltage value representing a difference between the output voltage before and after the converter is enabled (e.g., $V_1-V_2$). Note, $V_1$ is the no-load (open circuit) output voltage of the battery pack 45. $V_2$ is the output voltage of the battery circuit under load. $I_{load}$ is the load current as drawn by the converter when it is enabled. The internal resistance ($R_I$) 58 is then based on the following calculations:

$$R_I=(V_1-V_2)/I_{load}=\text{Stored delta voltage value}/I_{load}$$

As noted above, $R_I$ is inversely proportional to the load current. Thus, assuming that $I_{load}$ is the minimum converter current draw, a predetermined current value can be calculated as follows.

$$I_{loadmin}=\text{Converter current at maximum battery voltage } (12.75V)=2.15\text{ A}$$

Accordingly:

$$R_I=\text{Stored delta voltage}/2.15\text{ A}$$

In some examples, $R_I$ must be $<=0.9$ ohm, otherwise the battery pack may be deemed to be in need of service. At $R_I=0.9$ ohms, the stored delta voltage must be $<1935$ mV.

In an example, a predetermined $I_{load}$ current value (e.g., user-provided preset value) can be stored in a memory 36 accessible to controller 46 and used to determine the internal resistance of the one or more batteries 53 of the battery pack 45. For example, the predetermined current value can be chosen such that it is in a range of 2-3.5 amps. For example, the value can be selected to be 2.15 A. In some cases, the value can be selected to be 3 amps. For example, the particular predetermined current value can be selected as representative of the current drawn by converter 64 when charging capacitor bank 67. This amperage value may or may not be the actual current being drawn but, as noted above, it is representative and is selected based on statistical samples and/or engineering judgment as representative of the current drawn by converter 64 when charging capacitor bank 67 for the purpose of determining the internal resistance 58 of the one or more batteries 53 of battery pack 45. In some implementations, the battery pack may itself have a representation of the active current that can be drawn from the battery. As such, the current value for use in the calculations described herein can be determined from the battery pack based on such a representation.

In some implementations, it is also envisioned that a no load voltage of battery pack 45 ($V_{NL}$) can be measured and, separately, the output of battery pack 45 can be connected to a load resistor ($R_{load}$) and the voltage of the battery ($V_L$) connected to $R_{load}$ and the current ($I_L$) output by the battery to $R_{load}$ are measured. The internal battery resistance ($R_I$) is then determined from the formula: $R_I=(V_{NL}-V_L)\div I_L$, or an equivalent formula. In this latter example, the values of $V_{NL}$, $V_L$, and $I_L$ can be provided by battery circuit 56 to controller 46 which determines $R_I$ utilizing the foregoing formula, or any equivalent formula.

In some examples, the battery circuit 56 can track battery abuse. For example, battery abuse can be in the form of over-discharge, e.g., where the battery voltage is below a critical level that can be damaging or in some cases dangerous. Accordingly, the battery circuit 56 can detect an overdischarge condition when the battery is next placed in the device based on the detected voltage level. If the battery is deemed to have been overdischarged (e.g., in some embodiments, if the detected voltage transgresses some critical voltage threshold), this can trigger an internal impedance measurement. For example, the measurement can occur immediately after the battery is placed in the device and deemed to have been overdischarged. For example, the critical voltage threshold can be selected to be representative of the battery's particular chemistry and be determined on the basis of statistical samples and/or engineering experimentation as known to one skilled in the art.

The particular methods described herein of monitoring the battery condition, e.g., by determining the internal resistance 58 of the one or more batteries 53 of battery pack 45, however, are not to be construed as limiting inasmuch as it is envisioned that any means of determining the internal resistance 58 can be utilized. For example, the controller 46 can be configured to substantially uninterruptedly monitor the battery condition, e.g., by periodic measurements of internal resistance values, every 1-2 seconds. For example, the period can be adjusted by an operator to be more or less frequently that described herein. In some examples, the period can be an automatically adjustable parameter that is set such that when a battery is initially installed, the internal resistance measurements occur once every two weeks. After a certain passage of time of use of the battery in the medical device (e.g., 3-4 months), the controller 46 can automatically switch to begin checking the battery internal resistance once every week. As the battery resistance increases, more frequent checks can be automatically performed. In some situations, the device can be configured to reduce a frequency of internal resistance checks as the internal resistance of the battery reaches within a predetermined critical internal resistance range (e.g., between 0.7-0.9 ohms).

Figure 6:
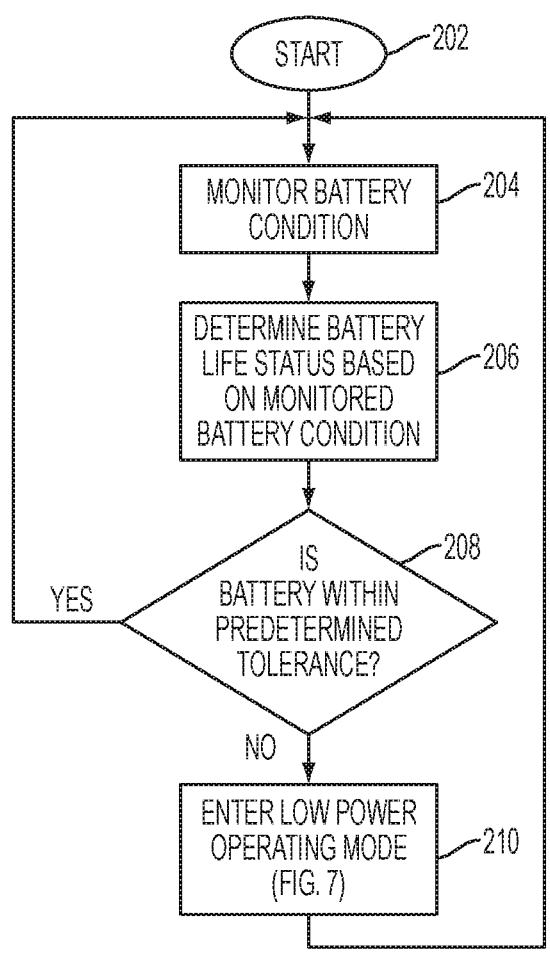
FIG. 6 is a flow chart of a method of operation where the external medical device enters a low power operating mode based on a monitored battery condition being outside of a predetermined tolerance or tolerance range.

Low Power Mode:

With reference to FIG. 6, in a method of determining whether or not to enter into a low power operating mode based on a monitored battery condition, the method advances from start step 202 to step 204 wherein controller 46 monitors the battery condition as described above. In step 206, controller 46 determines the battery life status (e.g., calculates the internal resistance 58 and projects remaining battery life) based on the monitored battery condition of batteries 53.

For example, the battery life status can be displayed on the user interface 70 of the monitor 5, a user interface of the dedicated standalone charger 62, or a user interface located at another convenient location. For example, the battery life status can be displayed along with a remaining amount of battery charge in the present battery charge-discharge cycle. In some situations, the battery life status can be transmitted to a remote location, (e.g., to remote server 78 for a technician located at a service center).

The method then advances to decision step 208 wherein controller 46 determines if the battery or batteries (i.e., the one or more batteries 53 of battery pack 45) are within a predetermined tolerance. In an example of determining battery life status, internal resistance 58 is determined. If in step 208 it is determined that that internal resistance 58 is <0.7 ohms (for example), controller 46 is programmed to deem this as the batteries 53 of battery pack 45 being within the predetermined tolerance, whereupon steps 204-208 may be repeated until, in an instance of step 208, controller 46 determines that the internal resistance 58 of the batteries 53 of battery pack 45 is not within (or has exceeded) the predetermined tolerance (in this example, 0.7 ohms). Upon determining that internal resistance 58 is ≥0.7 ohms (for example), controller 46 can be programmed to deem this as the batteries 53 of battery pack 45 are not within, or are outside of, (or have exceeded) the predetermined tolerance, whereupon the method advances to step 210 and controller 46 enters into a low power operating mode, described in greater detail hereinafter in connection with FIG. 7, in an effort to conserve battery power.

In this example, similar in manner to how the predetermined battery life threshold, indicative of battery 53 EOL status can be selected (e.g., in the example discussed herein, selected to be 0.9 ohms), the lower range of the predetermined critical range of 0.7 ohms can be selected as a representative value based upon statistical samples and/or engineering judgment. However, it is envisioned that one or more other resistance values can be selected in any manner deemed suitable and/or desirable by one of ordinary skill in the art.

In an example, determining the battery life status of the one or more batteries 53 can include determining a remaining amount of battery life based on a predetermined tolerance of internal resistance 58 associated with the battery, wherein the predetermined tolerance is defined by the battery life threshold expressed as a predetermined maximum internal resistance threshold of the one or more batteries beyond which the one or more batteries must be replaced. In an example, the predetermined tolerance of internal resistance 58 that triggers entering the low power operating mode (step 210) can be 0.7 ohms and the predetermined maximum internal resistance threshold indicative of battery 53 EOL status can be 0.9 ohms. A predetermined critical range can be within 0.7 to 0.9 ohms, for example. A person skilled in the art will readily recognize that the range of internal resistance values from 0.01 to 0.9 ohms can be divided into smaller ranges, each range associated with a different action that can be executed as described herein. For example, when the internal resistance falls within the predetermined critical range, as noted above, the device can enter a low power operating mode (step 210). In some implementations, the device can issue one or more alerts to the patient, caregiver, or remote center, that the internal resistance is in the predetermined critical range or has transgressed the predetermined maximum internal resistance threshold indicative of battery 53 EOL status. In some implementations, if the internal resistance is in the range of, for example, 0.6-0.7 ohms, the device can issue an alert to the patient, caregiver, or remote center, that the battery is nearing the predetermined critical range. In some implementations, the critical range can be configurable. In some implementations, the predetermined maximum internal resistance threshold and critical range can be dispensed with, whereupon, upon internal resistance 58 reaching the predetermined maximum internal resistance threshold indicative of battery 53 EOL status, the device changes its manner(s) of operation as described hereinafter without entering into low power operating mode (step 210).

Figure 7:
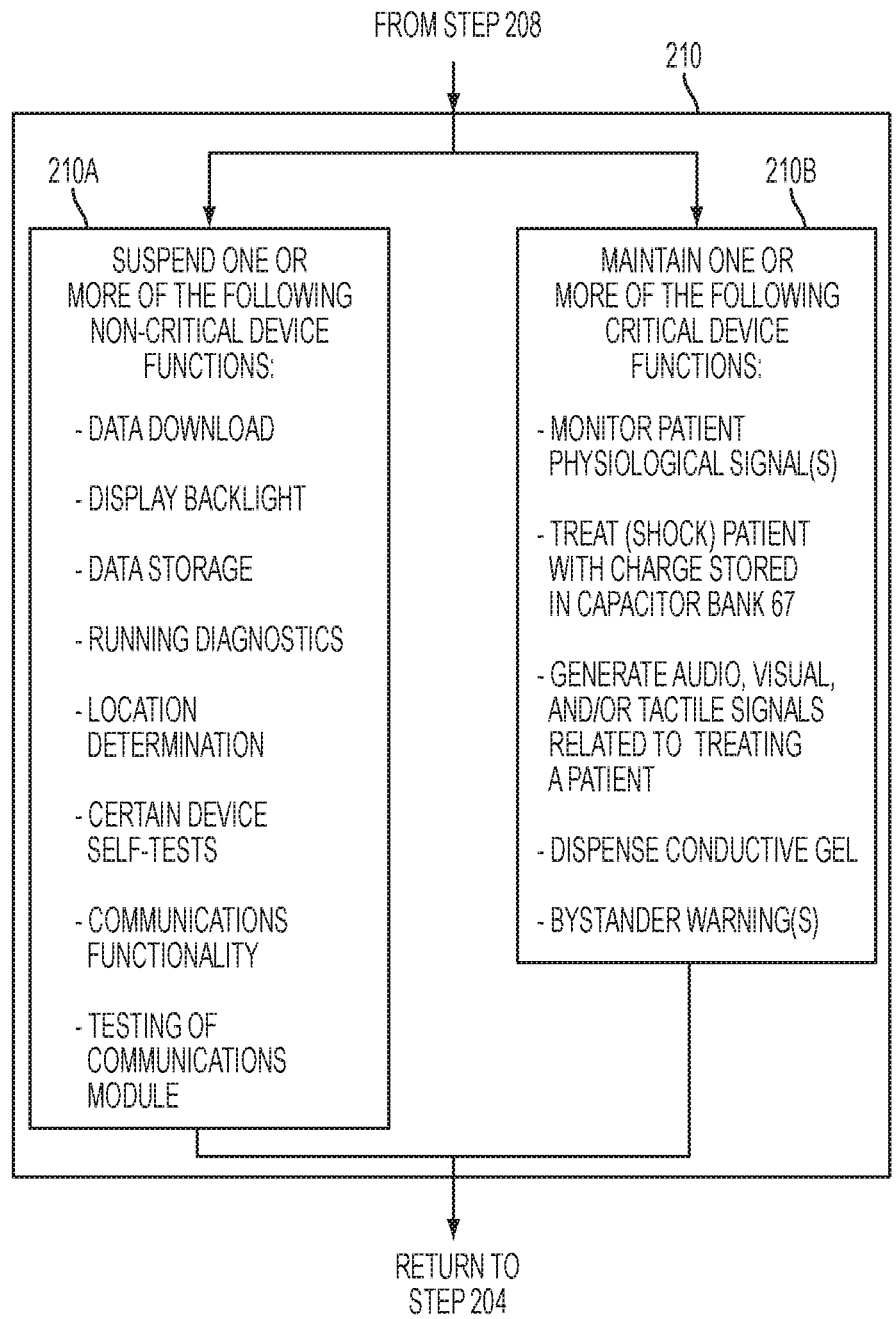
FIG. 7 shows internal details of the step of "Enter Low Power Operating Mode" in FIG. 6.

Low Power Mode Functions:

With reference to FIG. 7 and with continuing reference to FIG. 6, in an example of the low power operating mode, controller 46 suspends the performance of one, or more, or all non-critical device functions, such as, without limitation, data download, backlighting of display screen 43, running internal diagnostics, location determination via one or more communication devices of communication module 48, certain device self-tests, such as, without limitation, testing an ability of capacitor bank 67 to be charged, to hold a charge, and to be discharged, testing of communications functionalities, testing of the communication module, etc. In an example of the low power operating mode, however, controller 46 maintains some subset of one, or more, or all of the critical device functions, such as, without limitation, monitoring patient physiological signals, treating a patient with charge stored in capacitor bank 67, generating audio, visual, and/or tactile signals related to treating a patient, bystander warning(s), dispensing conductive gel 14, etc. The listing of these particular non-critical and critical functions, however, is not to be construed as limiting since it is envisioned upon determining battery life status and entering the low-power operating mode, that one or more non-critical functions can be maintained and/or one or more critical, but non-essential device functions can be suspended. Moreover, it is envisioned that a user, e.g., a technician, can override via, for example, user interface 70, the suspension of one or more of the non-critical functions and/or one or more critical, but non-essential device functions. In an example, the override of one or more of the non-critical functions and/or one or more critical, but non-essential, device functions can be accompanied by a user warning via user interface 70. In an example, the user can override the suspension of, for example, data download (which does not consume much power) while allowing controller 46 to suspend all other non-critical and critical device functions.

In an example, upon determining that internal resistance 58 is, for example, between 0.7 and 0.8 ohms, controller 46 may be programmed to suspend less than all of the non-critical device functions while maintaining some of the non-critical device functions. For example, controller 46 can be programmed to suspend display backlighting, running diagnostics, communications functionalities, testing of the communication module, and certain other device self-tests, but can be programmed to maintain data download, data storage, and location determination. Upon determining that internal resistance 58 is between 0.8 and 0.9 ohms, controller 46 can suspend all of the non-critical device functions. Upon determining that internal resistance 58 is ≥0.9 ohm (in this example, the predetermined maximum internal resistance threshold indicative of battery 53 EOL status), controller 46 can be programmed to suspend one or more critical, but non-essential device functions, such as generating audio, visual, and/or tactical signals related to treating a patient. Thus, as can be seen in this example, controller 46 can be programmed to progressively suspend device functions based upon the monitored internal resistance 58, with more functions being suspended as the one or more batteries 53 of battery pack 45 approach, meet, or exceed EOL status.

In the above description, a predetermined maximum internal resistance threshold of, for example, 0.9 ohms, is utilized as the predetermined battery EOL threshold. However, the use of other predetermined battery life thresholds is envisioned. In one example, controller 46 can track the total amount of time the one or more batteries 53 of a particular battery pack 45 are in use. In an example, each battery pack 45 utilized with monitor 5 can include a serial number. Controller 46 can be configured to read the serial number of each battery pack 45, either directly or via battery circuit 56, and can tally the total amount of time each battery pack 45 is in use via real time clock (RTC) 34 (shown in FIG. 4) of controller 46. Upon determining that the time that a particular battery pack 45 has been in use has reached a predetermined battery life threshold time or time interval, controller 46 can enter into the low power operating mode described above. In the manner described above for internal resistance 58, controller 46 can also or alternatively be programmed to suspend one or more non-critical and/or critical but non-essential device functions based upon the total amount of time a particular battery pack 45 has been in use.

In another example, controller 46 can be programmed to track the number of charge/discharge cycles of each battery pack 45 utilized with monitor 5 based upon a serial number of each battery pack 45 readable by controller 46 either directly or via battery circuit 56. For example, for each instance of battery pack 45 being installed in battery receptacle 47, controller 46 can be programmed to accumulate a count of each time the voltage output by the battery pack decreases from a predetermined upper operating voltage to a predetermined lower voltage, such decrease being indicative of a single charge/discharge cycle of battery pack 45. Upon accumulating a count of charge/discharge cycles equal to a predetermined count indicative of the predetermined battery life threshold, controller 46 can enter into the low power operating mode described above.

With reference to FIG. 8 and with continuing reference to FIGS. 3A, 4, 6, and 7, controller 46 can be programmed and operative for periodically (or aperiodically) performing a test of the one or more batteries 53 of battery pack 45. In this test, controller 46 causes converter 64 to fully charge capacitors 68 of capacitor bank 67 with electrical energy from battery pack 45. During this charging step, the internal resistance 58 of battery pack 45 is determined and is stored by controller 46 in the memory 36 of or accessible to controller 46. During each such battery test cycle, after being fully charged, the capacitors 68 of capacitor bank 67 are discharged through the energy dissipating element 73 (FIG. 4).

In an example, controller 46 can be programmed to accumulate and store in memory 36 a list of periodically (or aperiodically) determined internal resistances 58 along with dates the internal resistances were determined (see FIG. 8). As can be seen in FIG. 8, while the internal resistances 58 between adjacent samples can vary, the general trend is that the internal resistance 58 of battery pack 45 increases over time, as is known in the art. Based upon the trend of the changing internal resistance 58 obtained by the accumulated testing of battery pack 45, controller 46 can project, in advance, when internal resistance 58 will reach a predetermined internal battery resistance, e.g., 0.7 ohms, and can enter into the low power operating mode on this date without necessarily having to take a measurement of internal resistance 58 at that time.

The one or more batteries 53 of battery pack 45 can be conventional, dumb batteries (e.g., batteries that do not include built-in battery monitoring and/or management capabilities), or smart batteries (e.g., batteries that include one or more aspects of built-in battery monitoring and/or management capabilities). For example, battery monitoring and/or management circuitry included in a smart battery can measure battery voltage and current, and deduce charge level and state of health (SOH) of the battery.

In an example, the one or more batteries 53 or the battery pack 45 can include a portion of battery circuit 56. For instance, the one or more batteries 53 or the battery pack 45 can include circuitry for periodically or aperiodically (e.g., automatically in response to a triggering user action, a prior user configuration, or other event) monitoring the internal resistance 58 of one or more batteries 53 and storing an updated value of the internal resistance 58 in a register. Another portion of the battery circuit 56 disposed in, for example, a dedicated standalone battery charger 62 (FIG. 3B) or the monitor 5 can read, copy, or retrieve the internal resistance value stored in the register for use in accordance with the principles described herein.

Dedicated Charger Example:

Referring now to FIG. 3B and with continuing reference to FIGS. 3A and 4, in an example, wearable defibrillator 1 can be accompanied by a dedicated standalone charger 62. Dedicated charger 62 can include a battery charging circuit 60 that is configured in the nature of an AC-to-DC converter for converting incoming AC power provided via, for example, an AC wall socket, into DC power at an appropriate voltage and current level for charging the one or more batteries 53 when battery pack 45 is removed from battery receptacle 47 of monitor 5 and is installed in a battery pack receptacle 66 of dedicated charger 62. Dedicated charger 62 can also include a battery circuit 56' that is similar in function to battery circuit 56 of monitor 5 described above. Dedicated charger 62 can also include a controller 84 to which battery circuit 56' is coupled. Alternatively, battery circuit 56' can be part of controller 84. In use, battery circuit 56' monitors a condition of the one or more batteries 53 of battery pack 45 when battery pack 45 is supplying electrical current to a test load 82 via battery circuit 56'. In an example, test load 82 can be configured to approximate the load experienced by battery pack 45 under high current drain conditions (such as when battery pack 45 is charging capacitors 68) when installed in battery receptacle 47 of monitor 5.

Based on the voltage and/or current measurements taken by battery circuit 56' of battery pack 45 under simulated load conditions, controller 84 can determine a battery life status of the one or more batteries 53 of battery pack 45 in a manner similar to the way the battery life status of the one or more batteries 53 of battery pack 45 is determined by controller 46 of monitor 5.

Dedicated charger 62 can also include a battery life status notifier 86 that controller 84 can use to output a battery life status of the one or more batteries 53 of battery pack 45 when installed in battery pack receptacle 66. Battery life status notifier 86 can include one or more visual indicators (such as a display screen, LEDs, or other equivalent lamps) operating under the control of controller 84 for outputting a suitable visual indication of the battery life status of the one or more batteries 53 of battery pack 45. For example, if the battery life status of the one or more batteries 53 is determined to be within tolerance, controller 84 can cause battery life status notifier 86 to display a lamp or LED of a first color (green) or a first suitable notice on the display screen. Alternatively, if controller 84 determines that the battery life status of the one or more batteries 53 is out of tolerance, controller 84 can cause the battery life status notifier 86 to display a lamp or LED of a second color (red) or a second suitable notice on the display screen.

In another example, battery life status notifier 86 can also or alternatively include a speaker that can be operated under the control of controller 84 for outputting a suitable audio indication of the determined battery life status of the one or more batteries 53. For example, under the control of controller 84, a speaker of battery life status notifier 86 can output a notice "replace battery pack" in response to controller 84 determining that the batteries 53 of battery pack 45 are out of tolerance. Also or alternatively, operating under the control of controller 84, battery life status notifier 86 can output a suitable audio alert upon controller 84 determining that the batteries 53 of battery pack 45 are within tolerance, e.g., "battery pack within tolerance". In some examples, the battery life status notifier 86 can be in the medical device.

In an example, controller 84 can also, or alternatively, be operative for performing one or more of the following functions: maintaining a running total time that the one or more batteries 53 of battery pack 45 are in use; the number of charge/discharge cycles of battery pack 45; a table of periodic battery test results (see, e.g., FIG. 8); the estimated or actual internal resistance 58 of the one or more batteries 53 of battery pack 45; a difference between an estimated or measured internal resistance 58 and a predetermined maximum internal resistance threshold before the battery pack is deemed to require replacement; and/or whether the batteries 53 of battery pack 45 are within one or more predetermined ranges of internal resistance, e.g., the critical range discussed above, indicative of an impending need to replace battery pack 45 or a critical need to replace battery pack 45. In this regard, the foregoing functions of controller 84 and the functions of controller 46 of monitor 5 described above can be the same. In some examples, the battery life status notifier 86 can be located on the medical device (e.g., the monitor 5).

Example Battery Circuit:

Referring to FIG. 4, battery circuit 56 can be a standalone circuit, or can be part of a capacitor charging circuit 63 that also includes converter 64. In another example, battery circuit 56 can be part of controller 46. In another example, battery pack 45 can include all or part of battery circuit 56.

In another example, the components associated with battery circuit 56 can be standalone components, can be part of converter 64, can be part of controller 46, and/or can be part of battery pack 45. Hence, the illustration in FIG. 4 of battery circuit 56 as being a standalone element is not to be construed in a limiting sense. In one example, capacitor charging circuit 63 includes battery circuit 56 and converter 64. In another example (shown by dashed line 98 in FIG. 4) battery circuit 56 can be separate from charging circuit 63.

In an example, monitoring a condition of the battery includes battery circuit 56 monitoring a voltage of battery pack 45 during a predetermined time period and determining an internal resistance 58 of the one or more batteries 53 of battery pack 45 based on the monitored battery voltage. As discussed above, internal resistance 58 can be estimated by combining (dividing) the monitored delta battery voltage with an exemplary current value stored in memory 36 of controller 46. As discussed above, this exemplary current value is preselected based on statistical samples and/or engineering judgment to represent a typical current output by a typical battery pack 45 when converter 64 is charging capacitors 68 of capacitor bank 67 to a fully charged state from a low charge or discharged state. In an example, this exemplary current is 3.0 amperes. In another example, battery circuit 56 can be operative for measuring a no-load voltage ($V_{NL}$) of battery pack 45 and, separately, measuring the voltage ($V_L$) of the battery connected to a load resistor ($R_L$) and the current ($I_L$) output by the battery to the load resistor ($R_L$) and determining the internal resistance 58 of the battery ($R_I$) from the formula: $R_I=(V_{NL}-V_L)/I_L$, or an equivalent formula.

In an example, the predetermined time period that the battery voltage is monitored is the period of time for charging capacitors 68 of capacitor bank 67. In one example, the predetermined time period is within 2-35 seconds. In another example, the predetermined time period is within 15-20 seconds.

In another example, discussed above in connection with FIG. 8, monitoring the condition of the one or more batteries 53 of battery pack 45 includes periodically enabling the capacitor charging circuit 63 and, more particularly, converter 64, and determining internal resistance 58 of the one or more batteries 53 of battery pack 45 based on a current drawn by the capacitor charging circuit 63 from the one or more batteries 53 of battery pack 45.

In an example, the battery life status of the one or more batteries 53 of battery pack 45 can comprise determining a remaining amount of battery life based on a predetermined tolerance of internal resistance value associated with the one or more batteries 53. This predetermined tolerance can be defined by the battery life threshold expressed as a predetermined maximum internal resistance of the one or more batteries 53 beyond which the one or more batteries 53 must be replaced. In an example, this predetermined tolerance can be critical range (for example, between 0.7-0.9 ohms) discussed above. Finally, in another example, the predetermined maximum internal resistance threshold of the battery can be 0.9 ohms.

In yet another example, determining the battery life status of the one or more batteries 53 can comprise determining whether the monitored condition is outside of a predetermined tolerance range. For example, and as discussed above, controller 46 can be programmed with two or more predetermined tolerance ranges indicative of a level of urgency to replace battery pack 45. In another example, controller 46 can be programmed so that when the internal resistance 58 of the one or more batteries 53 is between 0.7 and 0.9 ohms, controller 46 outputs a notice that battery pack 45 should be replaced as soon as possible or within a predetermined period of time, e.g., two weeks. In another example, controller 46 can be programmed such that if the internal battery resistance 58 is ≥0.9 ohms, controller 46 outputs a notice that battery pack 45 requires replacement immediately.

In an example, upon entering the low power operating mode, controller 46 causes an output device, such as tactile simulator 12, speaker 21, visual indicator 25, and/or display screen 43, to output at least one of an audio, visual, and tactile alert in response to the determined battery life status. In another example, if the battery life status of the one or more batteries 53 is determined to require immediate replacement of battery pack 45, controller 46 can cause an audio, visual, and/or tactile alert to be output to inform the patient 9 of the need to replace battery pack 45.

In another example, controller 46 can be operative for causing communication module 48 to send a message concerning the battery life status to the remote server 78. This message can be that the battery life status of the one or more batteries 53 of battery pack 45 are within tolerance or out of tolerance.

Remote server 78 can be operative for storing each battery life status message received from communication module 48 in a file for wearable defibrillator 1 and can be further operative for causing a replacement battery pack 45 to be dispatched to the patient 9 in response to receiving a battery life status message that the current battery pack 45 is out of tolerance or is approaching EOL. Also or alternatively, remote server 78 can be operative for evaluating multiple battery life status messages received from communication module 48 for predicting when battery pack 45 will require replacement in advance of the one or more batteries 53 of battery pack 45 being deemed out of tolerance during a particular determination of the battery life status. In this regard, remote server 78 can be operative for dispatching a replacement battery pack 45 to the patient 9 in advance of the current battery pack 45 being deemed out of tolerance.

Figure 9:
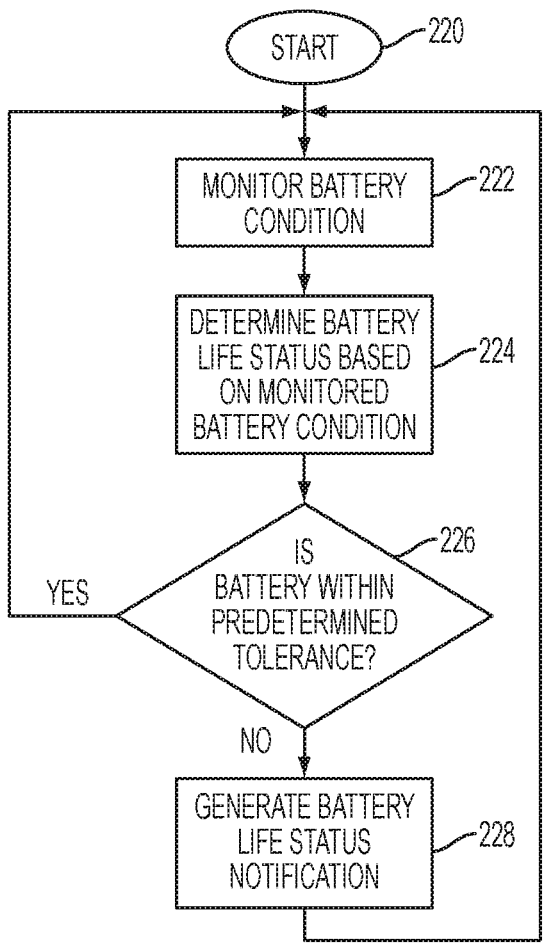
FIG. 9 is a flow chart of a method of operation where the external medical device generates a battery life status notification based on a monitored battery condition being outside of a predetermined tolerance or tolerance range.

Battery Life Status Notification:

With reference to FIG. 9 and with continuing reference to FIGS. 3A and 4, as discussed above, controller 46 can be operative (e.g., programmed) to output an audio, visual, and/or tactile alert when the battery life status is determined to be out of tolerance. For example, the notification can be provided via the monitor 5 of the external medical device, or the dedicated standalone charger 62 (FIG. 3B) when the battery pack 45 is inserted into the charger 62.

FIG. 9 shows example steps followed when generating a battery life status notification, in the form of an audio, visual, and/or tactile alert. Initially, the method advances from start step 220 to step 222 where the condition of the one or more batteries 53 of battery pack 45 is monitored, e.g., by battery circuit 56. The method then advances to step 224 wherein the battery life status is determined based on the monitored battery condition. In an example, this step can be performed by controller 46. Next, the method advances to decision step 226 where a determination is made whether the battery is within a predetermined tolerance, e.g., <0.7 ohms. In an example, this step can be performed by controller 46. If, in step 226 it is determined that the battery 53 is within the predetermined tolerance, steps 222, 224, and 226 are repeated until, in an instance of step 226 it is determined that the one or more batteries 53 (or battery pack 45) are outside of the predetermined tolerance whereupon the method advances to step 228. In step 228, a battery life status notification is generated. In an example, step 228 can occur under the control of controller 46. The battery life status notification output in step 228 can be output by any one or combination of tactile simulator 12, speaker 21, visual indicator 25, and/or display screen 43. Also, or alternatively, the battery life status notification that is generated in step 228 can be a message 90 dispatched from communication module 48 to remote sever 78.

Figure 10:
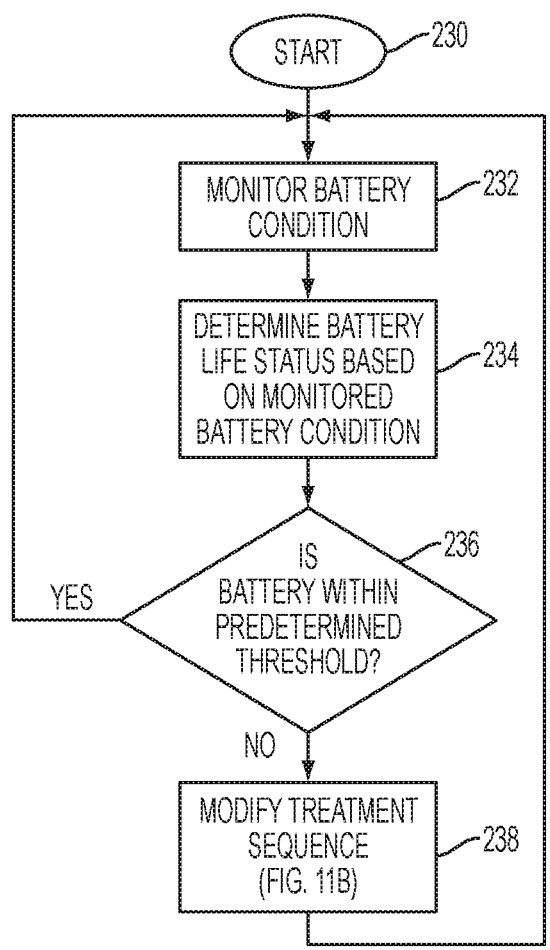
FIG. 10 is a flow diagram of a method of operation where the external medical device modifies a treatment sequence based on a monitored battery condition being outside of a predetermined tolerance or tolerance range.

Treatment Sequence Modification:

With reference to FIG. 10 and with continuing reference to FIGS. 3A and 4, in another example of a low power operating mode, when it is determined that the battery life status of the one or more batteries 53 of battery pack 45 are outside of a predetermined maximum internal resistance threshold indicative of battery EOL, the behavior of the circuitry of monitor 5 can be modified. For example, in a method of modifying circuit behavior, a sequence of how patient 9 is treated when an arrhythmia condition is detected can be modified. Specifically, the method shown in FIG. 10 commences by advancing from start step 230 to step 232 wherein the condition of the one or more batteries 53 of battery pack 45 are monitored. The method then advances to step 234 where the battery life status of the one or more batteries 53 is determined based on the monitored battery condition. Next, the method advances to decision step 236 wherein it is determined whether the one or more batteries 53 of battery pack 45 are within the predetermined tolerance, in this example, within the predetermined maximum internal resistance threshold. Steps 232, 234, and 236 may be repeated until, in an instance of step 236, it is determined that the one or more batteries 53 of battery pack 45 are outside of, .e.g., have exceeded, the predetermined tolerance, e.g., the predetermined maximum internal resistance threshold whereupon the method advances to step 238 wherein the treatment sequence by which patient 9 is treated when an arrhythmia is detected is modified. FIG. 11B shows an example modified treatment and charging sequence in comparison to a normal treatment and charging sequence shown in FIG. 11A.

Figure 11A:
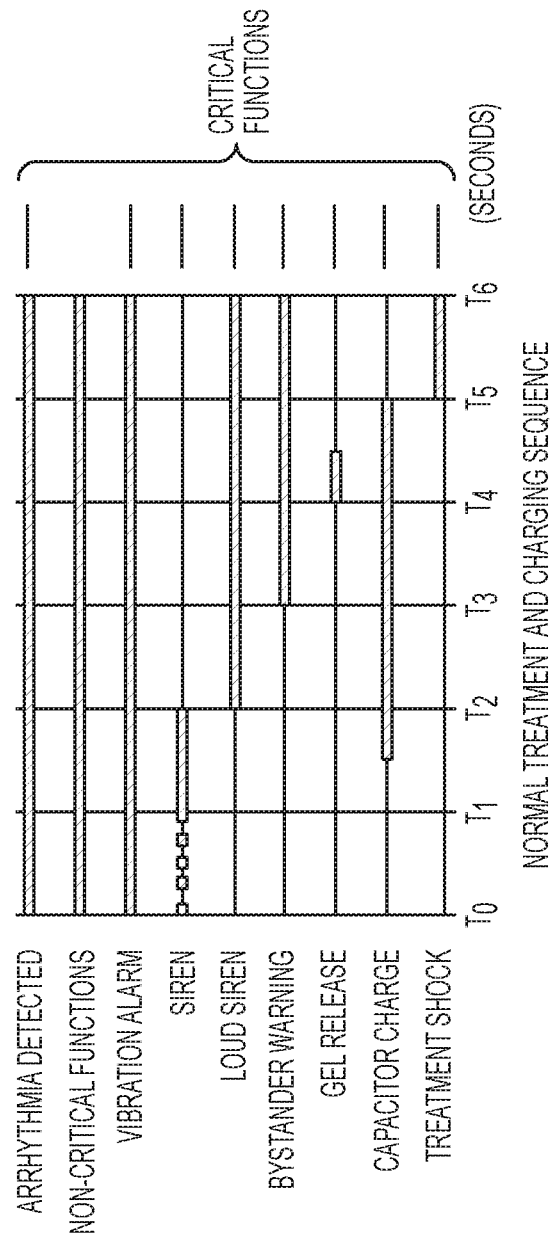
FIG. 11A is a graph of various non-critical and critical functions versus time for a normal patient treatment and capacitor charging sequence.
Figure 11B:
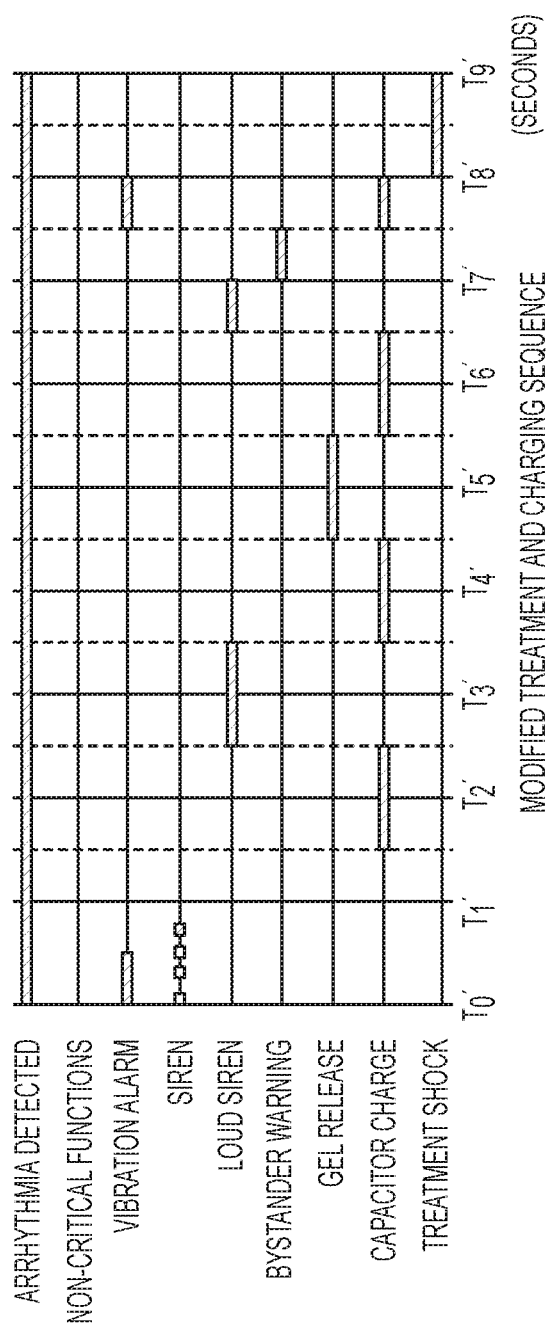
FIG. 11B is a flow diagram of a modified patient treatment and capacitor charging sequence.

In the normal treatment and charging sequence of FIG. 11A, which, in an example, would occur when the batteries 53 of battery pack 45 are within the predetermined tolerance, upon detecting an arrhythmia at time $T_0$ the patient 9 is alerted to the detected arrhythmia by way of a vibration alarm facilitated by tactile simulator 12 of monitor 5 being vibrated throughout the entire treatment sequence which extends, in this example, from time $T_0$ to time $T_6$. Between times $T_0$ and $T_1$, speaker 21 is caused to output a number of instances of siren sounds followed by an uninterrupted siren starting approximately at time $T_1$ and extending through time $T_2$. Starting at time $T_2$, speaker 21 is caused to output a loud siren sound that increases in volume between times $T_2$ and $T_6$. Starting between times $T_1$ and $T_2$, and ending at time $T_5$ the capacitors 68 of capacitor bank 67 are charged via converter 64 with electricity stored on battery pack 45. Between times $T_3$ and $T_6$, a bystander warning is caused to be output via speaker 21 in addition to the siren sound. This bystander warning may take the form of an audible prompt "bystanders, do not interfere". Between times $T_4$ and $T_5$, just prior to discharge module 42 being caused to apply a treatment shock to patient 9 with the charge stored on capacitors 68 of capacitor bank 67, electrolytic gel 14 is caused to be released between patient 9 and therapy pads 13a, 13b, 13c. Between times $T_5$ and $T_6$, a treatment shock is applied to patient 9 with the energy stored on capacitors 68 of capacitor bank 67.

As can be seen in FIG. 11A, when the batteries 53 of battery pack 45 are operating within the predetermined maximum internal resistance threshold, numerous critical and non-critical functions can be performed in parallel with the charging of capacitors 68. These numerous functions include non-critical functions (see, e.g., Step 210A in FIG. 7), siren and/or loud siren, bystander warning, gel 14 release, and arrhythmia detection.

In contrast, and as shown, for example in FIG. 11B, when the one or more batteries 53 are outside of their predetermined maximum internal resistance threshold, many of the functions performed in parallel with capacitor charging in FIG. 11A can be suspended in an effort to conserve battery power and the manner in which the one or more capacitors 68 of capacitor bank 67 are charged can be also modified.

In an example of circuit behavior modification, upon detection of an arrhythmia condition, the performance of one or all of the non-critical functions is suspended throughout the entire treatment sequence from time $T_0'$ through time $T_9'$. In FIG. 11B, the charging of the one or more capacitors 68 of capacitor bank 67 is broken into a series of charging steps (e.g., including a pause in charging between at least one pair of charging steps) occurring about times $T_2'$, $T_4'$, $T_6'$, and just prior to time $T_8'$, i.e., just prior to the application of the treatment shock between times $T_8'$ and $T_9'$. Each charging step can be the same or a different duration (or duty cycle) as deemed suitable and/or desirable in order to conserve the remaining power in the one or more batteries 53 of battery pack 45.

As can be seen in FIG. 11B, in a modified treatment and charging sequence, functions or activities, such as vibration alarm, siren, loud siren, bystander warning, and gel release can occur at times when a capacitor charging step is not being performed. For example, during a time when the capacitors 68 of capacitor bank 67 are being charged about time $T_2'$, noncritical functions, vibration alarm, siren, loud siren, bystander warning, and gel release are not performed. Between the first capacitor charging step about time $T_2'$ and the second capacitor charging step occurring about time $T_4'$, the loud siren warning is generated about time $T_3'$. During the second charging step about time $T_4'$, all of the functions not performed during the first charging step about time $T_2'$ are likewise not performed. Between the second charging step about time $T_4'$ and the third charging step around time $T_6'$, gel 14 is released about time $T_5'$ in preparation to apply the treatment shock between times $T_8'$ and $T_9'$. Between the third capacitor charging step about time $T_6'$ and the fourth capacitor charging step that occurs just prior to time $T_8'$, a loud siren is broadcast followed serially by a bystander warning. Between times $T_7'$ and $T_8'$ and partially overlapping the bystander warning and the fourth capacitor charging step, the vibration alarm is once again activated as a final warning to the patient of an impending treatment shock. Beginning at time $T_8'$, the fourth capacitor charging step is terminated and the treatment shock is applied until time $T_9'$.

It should be appreciated that one function that is not suspended between times $T_0'$ and $T_9'$, is the arrhythmia detection function. This is because, for example, if, at any time during the modified treatment and charging sequence, an arrhythmia condition is no longer detected, e.g., because the patient's heart has returned to normal rhythm, the modified treatment and charging sequence may be terminated and the device returns to a normal monitoring mode (see, e.g., FIG. 5).

In an example, the total time to charge the capacitors 68 of capacitor bank 67 runs about 15 seconds. However, this is not to be construed in a limiting sense. For instance, in FIG. 11A, the total time between $T_0$ and $T_6$ can run about 20 seconds. In FIG. 11B, the total time between $T_0'$ and $T_9'$ can run about 35 seconds, e.g., to accommodate the stepped or pulsed charging of one or more capacitors 68 of the capacitor bank 67.

FIG. 11B shows one example of a modified treatment and charging sequence. However, other modifications are envisioned. In an example, the duty cycle of the converter enable signal and, hence, the pulse or step charging of the capacitors 68 of capacitor bank 67 and/or the functions to be performed during or between each charging step can be modified if desired.

In various implementations, it is envisioned that, prior to use by a patient, the modified treatment sequence can be adjusted in accordance to one or more preferences specified by a user. For example, within a baselining and/or patient fitting context, a user can override the default converter duty cycle as needed, and/or adjust one or more other parameters of the modified treatment sequence.

In some implementations of modifying the treatment and charging sequence, the capacitors 68 are charged by pulsing the converter enable signal, e.g., the signal provided by controller 46 to converter 64, based on a predetermined duty cycle, e.g., a default duty cycle. Then, during step charging of the one or more capacitors 68, controller 46 can determine one or more functions to be performed along with an expected duration of the function. Next, based on the function determined to be performed, controller 46 can modify the converter enable signal to enable the thus determined function to be performed. In an example, the predetermined duty cycle can be fixed but the duration of the converter enable signal when the capacitors 68 are being charged can be modified to enable the function to be performed during the period when the converter enable signal is disabled. In an example, suppose the converter enable signal has a default duty cycle of 10 seconds—five seconds on and five seconds off. If, for example, controller 46 only requires two seconds to perform the gel 14 release function, controller 46 can modify the ten second converter duty cycle to 8 seconds on and 2 seconds off. During the time that the converter enables signal is off for 2 seconds, controller 46 can cause the gel 14 release function to be performed.

In some implementations, a user, via user interface 70, can override the default converter duty cycle for selected functions. For example, if the default converter duty cycle is 10 seconds—5 seconds on and 5 seconds off, it can be desirable under certain circumstances to allow a user, e.g., a technician, to override the default converter duty cycle for selected functions. For example, if it is desired to perform some combination of functions serially, in parallel, or some combination of serial and parallel, for more than 10 seconds, the default converter duty cycle can be overridden to permit this to occur while still enabling the capacitors 68 to be charged sufficiently to administer a treatment shock.

Figure 12:
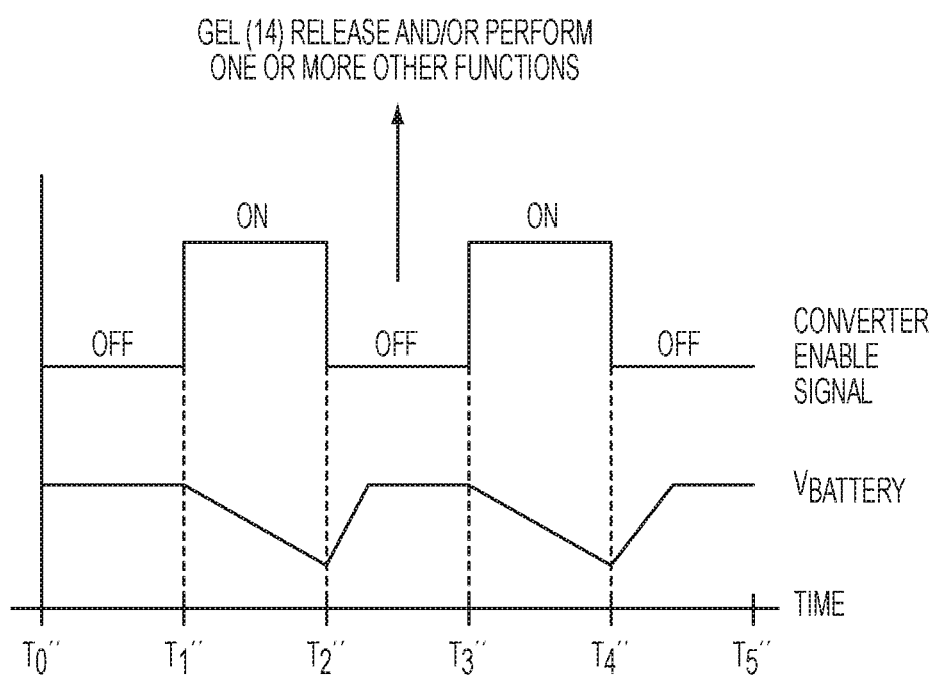
FIG. 12 is another example of a converter enable signal and voltage output by the battery pack shown in FIG. 4 versus time.

Charging and Charge Delivery Change:

With reference to FIG. 12 and with continuing reference to FIGS. 3A, 4, and 11B, in another representation of a modified treatment sequence, the one or more capacitors 68 are charged in pulsed steps as shown. In this modified treatment sequence, the battery life status is determined based on the monitored battery condition and a decision can be made if the battery life has reached or exceeded a predetermined battery life threshold (e.g., represented by predetermined internal resistance threshold value, e.g., 0.9 ohms), or a predetermined critical range, e.g., for internal resistance values, between 0.7 and 0.9 ohms. If so, the capacitor charging manner is modified. In one example, this modification includes modifying from continuously charging capacitors 68 during a charging sequence (as shown in FIG. 11A) to charging the capacitors 68 in steps or pulses (e.g., similar to that as shown in FIG. 11B). In one example, a single, fixed duty cycle can be utilized for charging the capacitors 68. In another example, the duty cycle used to charge the capacitors 68 during a charging sequence can be modified during the charging sequence. In yet another example, the on-time and off-time of each duty cycle can be modified (either alone or in combination with modifying the duty cycle) to enable the capacitors 68 to be charged as quickly as possible while enabling other functions, such as siren, loud siren, bystander warning, and/or gel release to occur during periods when the converter enable signal from controller 46 to converter 64 is disabled.

In the representation of a modified treatment sequence shown in FIG. 12, the converter enable signal from controller 46 to converter 64 is off or disabled between times $T_0''-T_1''$, $T_2''-T_3''$, and $T_4''-T_5''$. The converter enable signal is on or enabled between time $T_1''-T_2''$, and $T_3''-T_4''$. In an example, gel 14 can be released between times $T_2''-T_3''$ when the converter enable signal is off or disabled. In another example, one or more other critical and/or non-critical functions can also or alternatively be performed during any period when the converter enable signal is disabled. For example, depending on the charge state of the one or more batteries 53 of battery pack 45, the function of gel release can be accompanied by a loud siren and one or more non-critical functions, such as, for example, without limitation, data download.

For example, if, in response to the converter enable signal being disabled at time $T_2''$, the voltage of the one or more batteries 53 ($V_{battery}$) recovers quickly, indicative of the one or more batteries 53 not reaching EOL status, gel 14 release and one or more other critical and/or non-critical functions can be performed between times $T_2''-T_3''$. In another example, if, in response to the converter enable signal being disabled at time $T_2''$, the battery voltage does not recover rapidly, e.g., to a value less than $V_{battery}$ between times $T0''-T1''$ (indicative of the one or more batteries 53 approaching or being at EOL status) only gel 14 release may be performed and the remaining functions suspended. In this way, the functions performed each period of time the capacitors 68 are not being charged in the modified treatment and charging sequence of FIG. 11B can be dynamically tailored based upon how near or how far away the one or more batteries 53 of battery pack 45 are to EOL. The use of battery recovery as an indication of the health of the one or more batteries can be also or alternatively to the use of internal resistance, the total time that the one or more batteries 53 are in use, the number of charge/discharge cycles, and/or internal resistance trend.

Charge Capacitors from Backup Battery when Main Battery is Out of Tolerance

With ongoing reference to FIGS. 3A and 4, in an example, battery circuit 56, either alone or in combination with controller 46, can be operative for monitoring a battery voltage of battery pack 45 during charging of capacitors 68 of capacitor bank 67 from the one or more batteries 53 (i.e., main batteries 53 in battery back 45). In response to determining that battery life status (e.g., as represented through internal resistance 58) of main batteries 53 of battery pack 45 is outside of a predetermined maximum resistance threshold indicative of battery EOL, based on the monitored battery voltage, converter 64 can be caused to charge capacitors 68 from a backup battery 80 (shown in phantom in FIGS. 3A and 4) during a treatment sequence. In an example, backup battery 80 can be operative for charging one or more capacitors 68 at 2.5 amps for up to 30 seconds. However, this is not to be construed as limiting the invention. In an example, the backup battery 80 can be a lithium-ion battery. For example, the backup battery 80 can be rechargeable or non-rechargeable.

In some examples, the backup battery 80 may be disposed within a receptacle to allow a user to replace the backup battery 80. For instance, a mechanism may be provided to allow the user to release the backup battery 80 from its receptacle. In some examples, the backup battery 80 may be disposed within the housing of the monitor 5 in such a manner that the user is unable to remove/replace the backup battery 80 (e.g., the battery receptacle of monitor 5 that houses backup battery 80 is sealed and inaccessible to the user).

In an example, the combination of battery circuit 56 and controller 46 can be operative for determining when the main batteries 53, determined to have an internal resistance that is outside of (have exceeded) the predetermined maximum internal resistance threshold indicative of battery EOL, have been replaced with one or more replacement main batteries 53 having an internal resistance that is within the predetermined maximum internal resistance threshold. This can be accomplished, for example, by controller 46 periodically or occasionally causing the one or more capacitors 68 to be charged with batteries 53 installed in battery receptacle 47. If, during charging of capacitors 68, controller 46 determines that the internal resistance 58 of main batteries 53 is outside of the predetermined maximum internal resistance threshold, controller 46 causes converter 64 to charge the one or more capacitors 68 from backup battery 80. However, in an instance of periodically or occasionally attempting to charge the one or more capacitors 68 with main batteries 53 installed in battery receptacle 47, controller 46 determines that the internal resistance 58 of main batteries 53 is within the predetermined maximum internal resistance threshold (indicative of a change from main batteries 53 that are outside of (e.g., ≥) the predetermined maximum internal resistance threshold to main batteries 53 that are within (e.g., <) the predetermined maximum internal resistance threshold), controller 46 causes converter 64 to revert to charging capacitors 68 from the main, replacement batteries 53 rather than from the backup battery 80. The switching between charging capacitors 68 from main batteries 53 of the battery pack 45 or backup battery 80 can be automated. In some implementations, the backup battery 80 can be used to power all of the device's usual power requirements whenever the battery pack 45 is removed, e.g., for replacement.

In some implementations, during normal operations (e.g., when the device operates from the main batteries 53), the backup battery 80 can be recharged from the battery pack 45. For example, the backup battery 80 can be gradually recharged from the main battery over multiple charge-discharge cycles of the main batteries 53.

Store Charge on Capacitors Upon Detecting Battery Out of Tolerance

In an example, if it is determined via battery circuit 56 in combination with controller 46 during monitoring of the battery voltage of the one or more batteries 53 during charging of the capacitors 68 by converter 64 that the internal resistance 58 of the one or more batteries 53 is outside of (exceed) the predetermined maximum internal resistance threshold based on the monitored battery voltage, the one or more capacitors 68 can be isolated from the energy dissipating mechanism 73. In an example, and as discussed above, the energy dissipating mechanism 73 can include one or more discharge resistors or any component, system, or subsystem of monitor 5 that drains charge stored in the one or more capacitors 68 when not being used to treat a patient with charge stored in the one or more capacitors 68. In an example, the capacitor isolator (e.g., a switch) 88 can be coupled between capacitor bank 67 and the energy dissipating mechanism 73. Capacitor isolator 88 can be operated under the control of controller 46. In an example, in normal operation, when batteries 53 of battery pack 45 are within the predetermined maximum internal resistance threshold, capacitor isolator 88 operatively connects the one or more capacitors 68 to the energy dissipating mechanism 73 when it becomes necessary to dissipate the energy accumulated on the capacitors. In contrast, when batteries 53 are determined to be outside of (exceed) the predetermined maximum internal resistance threshold, the state of capacitor isolator 88 is controlled to isolate capacitors 68 from energy dissipating mechanism 73 to avoid draining the energy stored on the one or more capacitors 68.

In an example, the one or more capacitors 68 can be double layer capacitors or lithium-ion capacitors.

Operate Device with Charge Stored on Capacitors Upon Detecting Battery Out of Tolerance In an example, battery circuit 56, either alone or in combination with controller 46, can be operative for monitoring the battery voltage of the one or more batteries 53 during charging of capacitor 68 by converter 64. In response to determining that the one or more batteries 53 are outside of (exceed) the predetermined maximum internal resistance threshold based on the monitored battery voltage, a switching device 92 (FIG. 4) operating under the control of controller 46 can be switched whereupon one or more components, subsystems, or systems can revert from receiving power from the one or more batteries 53 to receiving power from capacitors 68 which are charged from main batteries 53 or, alternatively, backup battery 80. In an example, switching device 92 can be in a first state when the internal resistance 58 of the one or more batteries 53 are within the predetermined maximum internal resistance threshold to enable battery pack 45 to supply electrical power to one or more of controller 46, user interface 70, communication module 48, and/or belt node processor (BNP) 17. In an example, in response to determining that the one or more batteries 53 of battery pack 45 are outside of (exceed) the predetermined maximum internal resistance threshold based on the monitored battery voltage, switching device 92 can be switched to a second state under the control of controller 46 whereupon the one or more components, systems, or subsystems shown in FIG. 4 receive electrical power from capacitors 68 of capacitor bank 67. In an example, controller 46 can be operative for causing switching device 92 to revert back to the first state upon detecting that battery pack 45, including main batteries 53 that were determined to be outside of (exceed) the predetermined maximum internal resistance threshold has been replaced with a battery pack including main batteries 53 that are within the predetermined maximum internal resistance threshold.

In some implementations, when a cardiac event is detected (e.g., a cardiac arrhythmia condition) the device can cause the capacitors 68 to be charged. If the patient is conscious, he or she may suspend the therapeutic shock by holding down the response buttons 41 (e.g., if the condition is a false positive). In such a situation, for example, the capacitors may not be immediately discharged for a predetermined period of time in order to respond to a subsequent cardiac event. For example, this change in behavior may be effected if the device is operating in low power mode, modified treatment sequence mode, or if a battery has exceeded a predetermined battery life threshold, as described herein. For example, the predetermined period of time can be user-configured, e.g., in minutes or hours. For example, the period of time for which the capacitors may hold the charge can be up to an hour. If the patient goes into a real arrhythmia condition within an hour after the earlier event, then the charge on the capacitors may be readily deployed to shock the patient.

Battery Life Status Monitoring in a Patient Monitor

Figure 13:
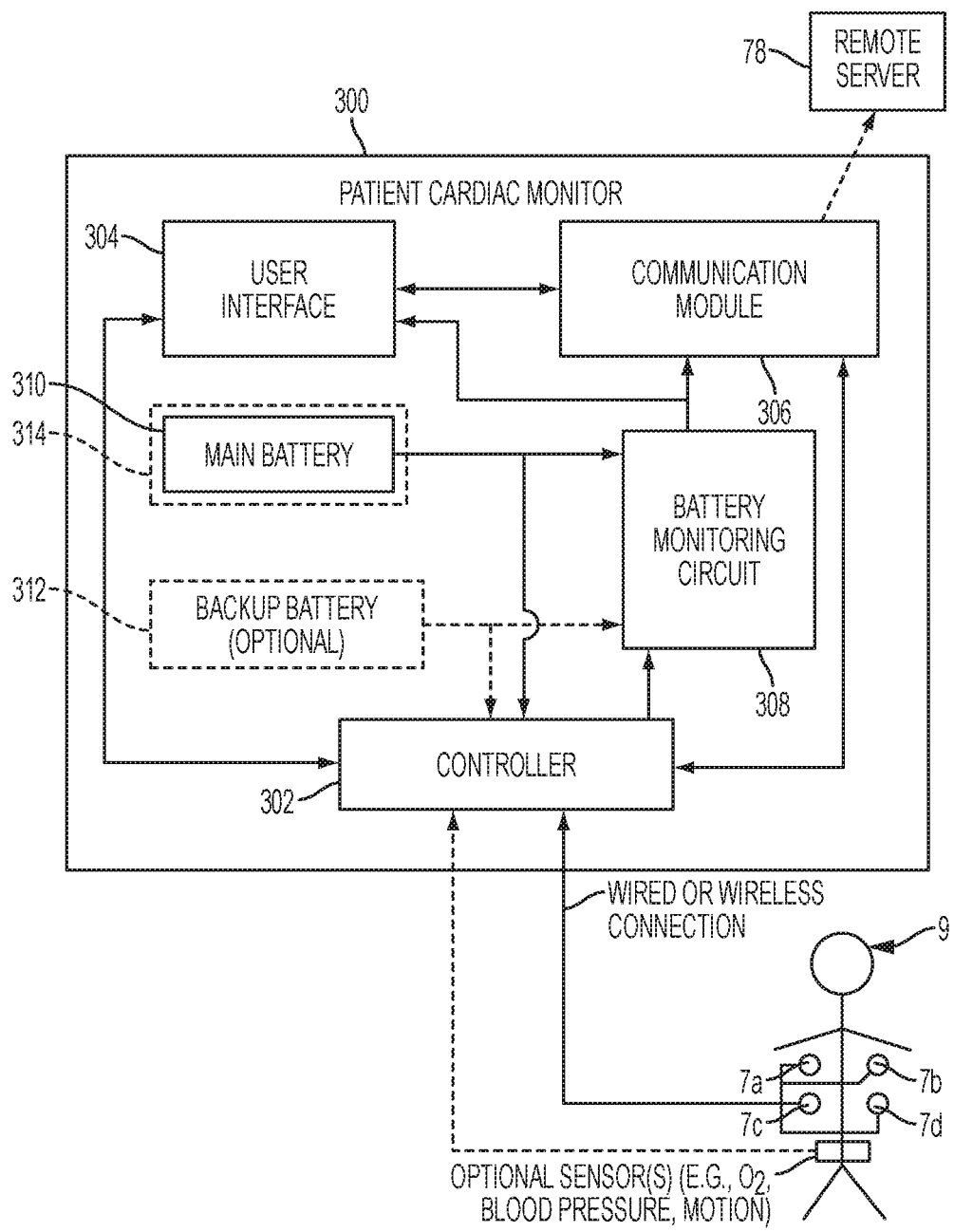
FIG. 13 is an example block diagram illustrating the functional components of a patient monitor (e.g., a cardiac monitor).

With reference to FIG. 13, it is envisioned that the external medical device as described herein can include a patient monitor 300, for example, a cardiac monitor. As such, the low power operating mode described herein can also be used in connection with the patient monitor 300. The monitor 300 can include a controller 302 that is communicatively coupled (e.g., wired or wirelessly coupled) to receive, from sensors and/or electrodes 7a-7d appropriately positioned on patient 9, signals (e.g., ECG data and/or heart sounds data from an acoustic sensor) indicative of cardiac activity of patient 9. In some examples, the sensors and/or electrodes can be an integral part of the housing structure of the patient monitor 300.

The patient monitor 300 can monitor either or both cardiac-related patient parameters and/or other physiological information or parameters, such as, without limitation, patient symptom data (e.g., patient-reported symptoms and/or automatically detected patient information), related cardiac data including premature ventricular contraction (PVC) count, heart rate information, heart sounds data, ECG data (e.g., continuous ECG data), lung fluid measurements/data, patient thoracic impedance measurements/data, and pectoral impedance measurements/data. For example, the ECG data can be associated with the patient symptom data. For example, up to a one minute or more ECG recording can be associated with one or more patient-reported symptoms, as described in further detail below. For example, the physiological data may be pre-tagged by the user (e.g., the patient) prior to transmission. In an example, the patient can input one or more annotations relating to the physiological information that is then transmitted along with the physiological information. In some examples, the patient monitor 300 can monitor blood pressure, temperature, blood glucose levels, and blood oxygen levels. In some examples, the patient monitor 300 can monitor sleep data. For example, the patient monitor 300 may receive and/or sense information relating to sleep apnea, an indication of a time when the patient goes to sleep, and/or sleep data covering a period of time during which the patient is asleep, such as ECG data, heart and lung sounds, respiration, etc. In some examples, the patient monitor 300 can include motion sensors to track patient movement.

For example, the patient monitor 300 can be in the form of an application on a handheld device, such as a smartphone, a personal digital assistant, or a tablet device. In such implementations, the battery management techniques described herein can be used in connection with monitoring the battery life status of the battery of the smartphone, personal digital assistant, or tablet device.

As shown, the patient monitor 300 can communicate with remote server 78 (e.g., one or more computer systems). For example, the patient monitor 300 may communicate with another device which may be a remote handheld device (e.g., a smartphone, a personal digital assistant, or a tablet device). For example, the patient monitor 300 may periodically (e.g., on a preset schedule) and/or aperiodically (e.g., when prompted by a user or an external event) establish a wireless communication (e.g., cellular communication, WiFi, or Bluetooth) to transfer patient data to the remote server 78. For example, one or more such communications can be delayed, e.g., due to latencies in the signal processing circuitry and/or a user configurable delay.

In an example, patient monitor 300 can include a user interface 304, a communications module 306, and a battery monitoring circuit 308 coupled to controller 302. A main battery 310 and an optional backup battery 312 can be used to supply electrical power for the operation of controller 302, user interface 304, communications module 306, and battery monitoring circuit 308. Main battery 310 can be a rechargeable battery that is received in a battery receptacle 314 of patient monitor 300. In some examples, the main battery 310 may be disposed within the monitor 300 in such a manner that the user is unable to remove/replace the battery (e.g., the battery receptacle 314 is sealed and inaccessible to the user). Optional backup battery 312 can be a rechargeable battery or a single use battery.

Battery monitoring circuit 308 can be operative under the control of controller 302 for determining a battery life status of main battery 310 in accordance with the principles described herein. In some examples, the battery life status can be displayed on the user interface 304 via a battery life status identifier, in addition to a remaining charge within a given charge-discharge cycle. For instance, any of the underlying battery life status identifiers can be displayed on the user interface 304 as the battery life status notification, e.g., a numerical or graphical representation of the internal resistance of the battery, an amount of time, or a number of charge-discharge cycles remaining, an elapsed or a remaining number of ampere-hours, or a function based on one or more of the foregoing. Further, notifications and/or alerts can be set on the monitor 300 based on battery life status information. In some cases, the notifications and/or alerts can be user configurable. In some situations, one or more notifications and/or alerts can be preprogrammed into the monitor 300.

In an example, battery monitoring circuit 308 can be operative under the control of controller 302 for measuring a no load voltage ($V_{NL}$) of battery 310 and for providing a suitable indication of the measured value of $V_{NL}$ to controller 302. In one example of measuring $V_{NL}$ of main battery 310, user interface 304 and communications module 306 can be isolated from main battery 310 during at least the time that $V_{NL}$ is being measured by battery monitoring circuit 308. In another example of measuring $V_{NL}$ of main battery 310, power consumption in user interface 304 and/or communications module 306 can be minimized, e.g., by controller 302 setting user interface 304 and/or communications module 306 in a state that minimizes power consumption. In these examples, $V_{NL}$ is an estimate of the no load voltage of main battery 310 since main battery 310 is supplying electrical power to at least controller 302 and battery monitoring circuit 308 during measurement of a value representative of $V_{NL}$.

In another example of measuring $V_{NL}$ of main battery 310, controller 302, user interface 304, communications module 306, and battery monitoring circuit 308 can be switched to receiving operating power from backup battery 312, and main battery 310 can be isolated from supplying operating electrical power to controller 302, user interface 304, communications module 306, and battery monitoring circuit 308. Thereafter, operating with electrical power from backup battery 312, controller 302, and battery monitoring circuit 308 can measure $V_{NL}$ of main battery 310.

Separately to determining $V_{NL}$, main battery 310 can be connected to a test load ($R_{load}$) of battery monitoring circuit 308 and the load voltage ($V_L$) of battery 310 connected to $R_{load}$ and the load current ($I_L$) output by battery 310 to $R_{load}$ can be measured by battery monitoring circuit 308 and supplied to controller 302 for processing. In one example of measuring $V_L$ and $I_L$, main battery 310 can be isolated from supplying operating electrical power to controller 302, user interface 304, communications module 306, and battery monitoring circuit 308 and, at least for the duration of the determining the values of $I_L$ and $V_L$, controller 302 and battery monitoring circuit 308 can receive operating electrical power from backup battery 312. In another example, the value of $R_{load}$ (typically a low resistance value ≤1 ohm or ≤10 ohms) can be in parallel with input resistances/impedances of one or more of controller 302, user interface 304, and/or communications module 306, whereupon the effective resistance seen by the output of main battery 310 during measurement of values for IL and $V_L$ is approximately $R_{load}$.

The thus determined values of $I_L$ and $V_L$ can be used by controller 302 to determine the internal battery resistance ($R_I$) of battery 310 from the formula: $R_I=(V_{NL}-V_L)\div I_L$, or an equivalent formula. In this example, the values of $V_{NL}$, $V_L$, and $I_L$ can be provided by battery monitoring circuit 308 to controller 302, which determines $R_I$ utilizing the foregoing formula, or any equivalent formula.

In response to determining that the value of $R_I$ of main battery 310 has reached a predetermined maximum internal resistance threshold value, e.g., 0.9 ohms, or a predetermined critical range, e.g., between 0.7 and 0.9 ohms, indicative of actual or approaching EOL of main battery 310, controller 302 can cause patient monitor 300 to modify the behavior of circuitry of patient monitor 300, or enter into a low power operating mode that can include modifying the behavior of circuitry of patient monitor 300.

In an example of entering into low power operating mode in response to determining that $R_I$ is in the predetermined critical range or has reached the predetermined maximum internal resistance threshold, controller 302 can suspend one, or more, or all of the features of user interface 304 such as, without limitation, suspend the continuous use of a display of user interface 304 and/or suspend the continuous illumination of one or more lamps (LED's) of user interface 304. Also or alternatively, controller 302 can cause user interface 304 to periodically or occasionally (e.g., aperiodically) output a signal detectable by the patient 9 using patient monitor 300 that the main battery 310 requires replacement. This signal can take the form of a visual indication on a display of user interface 304 or the illumination of one or more lamps of user interface 304.

In a normal mode of operation of patient monitor 300 when $R_I$ is <the predetermined critical range and/or <the predetermined maximum internal resistance threshold value, communication module 306 can be operative for periodically or occasionally (e.g., aperiodically) acquiring the patient's ECG signal or data and transmitting to remote server 78 one or more messages, each of which can include one or more of the following: one or more cycles or sub cycles of the acquired patient's ECG signal or data; an indication that the patient's ECG signal or data is within or outside of one or more predetermined limits (e.g., as determined by controller 302); and/or a state of health of main battery 310. Upon entering the low power operating mode, it is envisioned that the duration of the periodic or occasional acquisition of the patient's ECG signal or data and/or the duration of the periodic or occasional (aperiodic) transmission of such messages can be extended (versus the duration(s) in the normal mode of operation of patient monitor 300) in an attempt to conserve main battery power. For example, if communications module 306 can use cellular communication, WiFi, or Bluetooth (via, for example, a smart phone of patient 9) to transmit messages to remote server 78 when $R_I$ is <the predetermined critical range and/or the predetermined maximum internal resistance threshold value, upon entering into the low power mode, the use of cellular communication can be suspended, and communications can be limited to either or both of WiFi and/or Bluetooth communications.

Also or alternatively, controller 302 can be programmed to progressively suspend functions as the value of $R_I$ if main battery 310 approaches the EOL status. For example, for $R_I$ determined to be between 0.7 and 0.8 ohms, controller 302 can suspend the use of one or more functions of user interface 304, or cause periodic or occasional (aperiodic) use of these one or more functions. When $R_I$ is determined to be between 0.8 and 0.9 ohms, controller 302 can permanently suspend the use of all functions of user interface 304 and can increase the duration that the patient's ECG signal or data are acquired and/or the duration that messages are transmitted to remote server 78 over the duration(s) in the normal mode of operation of patient monitor 300.

Finally, in an example, in response to determining that the value of $R_I$ of main battery 310 has reached the predetermined maximum internal resistance threshold value indicative of EOL of main battery 310, controller 302, user interface 304, communications module 306, and battery monitoring circuit 308 can be switched to receiving operating power from backup battery 312. Also, or alternatively, when running on power from backup battery 312, controller 302 can cause user interface 304 to periodically or occasionally output a signal detectable by the patient 9 using patient monitor 300 that main battery 310 requires replacement. This signal can take the form of a visual indication on a display of user interface 304 or the illumination of one or more lamps of user interface 304.

The embodiments have been described with reference to various examples. Modifications and alterations will occur to others upon reading and understanding the foregoing examples. Accordingly, the foregoing examples are not to be construed as limiting the disclosure.

The invention claimed is:

1. An external medical device, comprising:
a battery that can support a plurality of charge-discharge cycles prior to a predetermined battery life threshold; and
a battery circuit operative for:
monitoring a condition of the battery;
determining a battery life status of the battery based on the monitored condition and the predetermined battery life threshold; and
responsive to the determined battery life status, causing the device to enter into a low power operating mode,
wherein causing the device to be operated in the low power operating mode comprises causing the device to perform predetermined critical device operations and turning off predetermined non-critical device operations.

2. The external medical device of claim 1, wherein monitoring the condition of the battery comprises monitoring an internal resistance of the battery.

3. The external medical device of claim 1, further comprising:
one or more capacitors operative for storing charge; and
a capacitor charging circuit operative for causing the battery to charge the one or more capacitors.

4. The external medical device of claim 3, wherein the capacitor charging circuit comprises a voltage converter.

5. The external medical device of claim 3, wherein monitoring the condition of the battery comprises periodically enabling the capacitor charging circuit and determining an internal resistance of the battery based on a current drawn by the capacitor charging circuit from the battery.

6. The external medical device of claim 1, wherein monitoring the condition of the battery comprises monitoring a battery voltage during a predetermined time period and determining an internal resistance of the battery based on the monitored battery voltage.

7. The external medical device of claim 6, wherein the predetermined time period comprises a period of time for charging a capacitor.

8. The external medical device of claim 6, wherein the predetermined time period is within 2-35 seconds.

9. The external medical device of claim 1, wherein determining the battery life status of the battery comprises determining a remaining amount of battery life based on a predetermined tolerance of internal resistance values associated with the battery, wherein the predetermined tolerance is defined by the predetermined battery life threshold expressed as a predetermined maximum internal resistance threshold of the battery beyond which the battery must be replaced.

10. The external medical device of claim 9, wherein the predetermined tolerance of internal resistance values is within a range of 0.1 to 0.7 ohms.

11. The external medical device of claim 9, wherein the predetermined maximum internal resistance threshold of the battery is 0.9 ohms.

12. The external medical device of claim 1, wherein the predetermined non-critical device operations comprise one or more of data download; display backlight; data storage; running diagnostics; location determination; certain device self-tests; communications functionality; and/or testing of communications module.

13. An external medical device, comprising:
a battery that can support a plurality of charge-discharge cycles prior to a predetermined battery life threshold; and
a battery circuit operative for:
monitoring a condition of the battery;
determining a battery life status of the battery based on the monitored condition and the predetermined battery life threshold; and
responsive to the determined battery life status, causing the device to enter into a low power operating mode,
wherein causing the device to be operated in the low power operating mode comprises causing the device to change a treatment sequence of the device, and
wherein causing the device to change the treatment sequence comprises, as a first action of one or more actions, periodically enabling and disabling a charging circuit for charging one or more capacitors, and causing the device to perform a second action of the one or more actions during a period when the charging circuit is disabled.

14. The external medical device of claim 13, wherein changing the treatment sequence includes at least one of:
suspending performance of at least one non-critical function; and
suspending performance of at least one critical function during performance of the first action.

15. The external medical device of claim 14, wherein,
the at least one non-critical function comprises data download, display backlight, data storage, running diagnostics, location determination, certain device self-tests; communications functionality; and/or testing of communications module; and
the at least one critical function comprises monitor patient physiological signals, treat a patient with charge stored in the one or more capacitors, generate audio, visual, and/or tactile signals relating to treating the patient, bystander warning(s), and/or dispensing conductive gel.

16. A battery circuit for use with an external medical device, comprising:
a battery receptacle configured to receive a battery that can support a plurality of charge-discharge cycles prior to a predetermined battery life threshold; and
the battery circuit operative for:
monitoring a condition of the battery;
determining a battery life status of the battery based on the monitored condition and the predetermined battery life threshold; and
responsive to the determined battery life status, causing a battery life status notification to be generated,
wherein monitoring the condition of the battery comprises monitoring a battery voltage during a predetermined time period and determining an internal resistance of the battery based on the monitored battery voltage, and wherein the predetermined time period is within 2-35 seconds.

17. An external medical device, comprising:
a battery that can support a plurality of charge-discharge cycles prior to a predetermined battery life threshold; and
a battery circuit operative for:
monitoring a condition of the battery;
determining a battery life status of the battery based on the monitored condition and the predetermined battery life threshold; and
responsive to the determined battery life status, causing the device to enter into a low power operating mode,
wherein determining the battery life status of the battery comprises determining a remaining amount of battery life based on a predetermined tolerance of internal resistance values associated with the battery, wherein the predetermined tolerance is defined by the predetermined battery life threshold expressed as a predetermined maximum internal resistance threshold of the battery beyond which the battery must be replaced, and
wherein the predetermined tolerance of internal resistance values is within a range of 0.1 to 0.7 ohms.

18. The external medical device of claim 17, wherein the predetermined maximum internal resistance threshold of the battery is 0.9 ohms.

* * * * *